US010584094B2

(12) United States Patent
Voronov et al.

(10) Patent No.: US 10,584,094 B2
(45) Date of Patent: Mar. 10, 2020

(54) BIO-BASED ACRYLIC MONOMERS AND POLYMERS THEREOF

(71) Applicants: Andriy Voronov, Reiles Acres, ND (US); Ihor Tarnavchyk, West Fargo, ND (US)

(72) Inventors: Andriy Voronov, Reiles Acres, ND (US); Ihor Tarnavchyk, West Fargo, ND (US)

(73) Assignee: NDSU RESEARCH FOUNDATION, Fargo, ND (US)

( * ) Notice: Subject to any disclaimer, the term of this patent is extended or adjusted under 35 U.S.C. 154(b) by 0 days.

(21) Appl. No.: 16/395,755

(22) Filed: Apr. 26, 2019

(65) Prior Publication Data

US 2019/0248735 A1    Aug. 15, 2019

Related U.S. Application Data

(62) Division of application No. 15/502,342, filed as application No. PCT/US2015/044288 on Aug. 7, 2015, now Pat. No. 10,315,985.

(60) Provisional application No. 62/035,114, filed on Aug. 8, 2014.

(51) Int. Cl.
| | |
|---|---|
| C07C 233/20 | (2006.01) |
| C08F 220/58 | (2006.01) |
| C09D 133/24 | (2006.01) |
| C07C 231/12 | (2006.01) |
| C09D 133/26 | (2006.01) |

(52) U.S. Cl.
CPC .......... C07C 233/20 (2013.01); C07C 231/12 (2013.01); C08F 220/58 (2013.01); C09D 133/24 (2013.01); C09D 133/26 (2013.01)

(58) Field of Classification Search
CPC ... C07C 233/20; C07C 231/12; C08F 220/58; C09D 133/24; C09D 133/26
USPC ........................................................ 524/555
See application file for complete search history.

(56) References Cited

U.S. PATENT DOCUMENTS

| | | | |
|---|---|---|---|
| 2,692,256 A | 10/1954 | Bauer et al. | |
| 3,887,609 A | 6/1975 | Strehlke et al. | |
| 5,338,471 A * | 8/1994 | Lal ..................... | C10M 169/044 44/403 |
| 6,080,480 A * | 6/2000 | Shiba .................... | C09J 123/20 428/355 R |
| 6,174,948 B1 | 1/2001 | Thames et al. | |
| 7,378,479 B2 | 5/2008 | Tamareselvy et al. | |
| 7,910,680 B2 | 3/2011 | White et al. | |
| 8,450,414 B2 | 5/2013 | Thames et al. | |
| 2008/0183000 A1 | 7/2008 | Thames et al. | |

FOREIGN PATENT DOCUMENTS

| | | |
|---|---|---|
| DE | 10 2008 002254 A1 | 1/2010 |
| WO | WO 2011/060293 A1 | 5/2011 |
| WO | WO 2016022960 A2 | 2/2016 |
| WO | WO 2016022960 A9 | 2/2016 |

OTHER PUBLICATIONS

Maiti et al. "RAFT polymerization of fatty add containing monomers: controlled synthesis of polymers tram renewable resources", RSC Adv., 2013, 3, 24983 (Year: 2013).*
International Search Report and Written Opinion for PCT/US2015/044288, dated Mar. 24, 2016, 10 pages.
International Preliminary Report on Patentability PCT/US2015/044288, dated Feb. 23, 2017, 8 pages.
Supplementary European Search Report, European Application No. 15 82 9462, dated Mar. 14, 2018, 11 pages.
Aigbodion et al., "Utilisation of maleinized rubber seed oil and its alkyd resin as binders in water-borne coatings," Prog Org Coat, Jan. 2003, 46(1):28-31.
Asadauskas et al., "Thin-Film Test to Investigate Liquid Oxypolymerization of Nonvolatile Analytes: Assessment of Vegetable Oils and Biodegradable Lubricants," J Am. Oil Chem. Soc., Jan. 2001, 78(10):1029-1035.
Bailey, A.E., "Bailey's Industrial Oil and Fat Products," 1996, Wiley, New York.
Belgacem et al., "Monomers, Polymers and Composites from Renewable Resources," Elsevier, 2008, Amsterdam, Netherlands, 562 pages.
Biermann et al., "New Syntheses with Oils and Fats as Renewable Raw Materials for the Chemical Industry," Angew. Chem. Int. Ed. Engl., Jul. 3, 2000, 39(13):2206-2224.
Brekke et al., "Nonconjugated linseed vinyl ether by vinyl transetherification. Preparation procedure," J. Am. Oil Chemists' Soc., Nov. 1960; 37(11):568-570.
Bunker et al., "Synthesis and characterization of monomers and polymers for adhesives from methyl oleate," J. Polym. Sci., Part A: Polym. Chem., Feb. 15, 2002; Epub Jan. 4, 2002; 40(4):451-458.
C.E. Carraher, Introduction to Polymer Chemistry, 2nd edition, 2010, Taylor & Francis, CRC Press, Boca Raton, FL., publisher page and Table of Contents.
çayli et al., "Polymers from renewable resources: Bulk ATRP of fatty alcohol-derived methacrylates," Eur. J. Lipid Sci. Technol., Sep. 18, 2008, 110(9):853-859.

(Continued)

*Primary Examiner* — Michael Bernshteyn
(74) *Attorney, Agent, or Firm* — Meuting, Raasch & Gebhardt, P.A.

(57) ABSTRACT

The invention provides a bio-based acrylic monomer, particularly a plant oil-based acrylic monomer, which is well-suited for emulsion polymerization and latex formation in aqueous medium. Polymers and copolymers formed from the bio-based acrylic monomer are also provided. The invention further provided methods for making the monomer from bio-based triglycerides or fatty esters.

19 Claims, 11 Drawing Sheets

(56) References Cited

OTHER PUBLICATIONS

Chanda, M. Introduction to Polymer Science and Chemistry: A Problem Solving Approach, 2006, Taylor & Francis, CRC Press, Boca Raton, FL., publisher page and Table of Contents.
Derksen et al., "Renewable resources in coatings technology: a review," *Prog. Org. Coat*, Jan.-Apr. 1996, 27(1-4):45-53.
Eren et al., "Synthesis and characterization of copolymers of bromoacrylated methyl oleate," *J. Appl. Polym. Sci.*, Dec. 15, 2004; Epub Oct. 25, 2004; 94(6):2475-2488.
Eren et al., "Synthesis and polymerization of the acrylamide derivatives of fatty compounds," *J. Appl. Polym. Sci.*, Sep. 15, 2005, 97(6):2264-2272.
Erkal et al., "Styrenation of triglyceride oils by macromonomer technique," *J Coat. Technol.* Dec. 1993, 65(827):37-43.
Gallezot, "Conversion of biomass to selected chemical products," *Chem. Soc. Rev.*, 2012, 41:1538-1558.
Guner et al., "Styrenation of Triglyceride Oils by Macromonomer Technique," *Journal of Coatings Technology*, Aug. 2000; 72(907):107-110.
Guner et al., "Polymers from triglyceride oils.," *Prog. Polym. Sci.*, 2006, 31:633-670.
Gunstone, F.D. "Fatty acid and lipid chemistry," 1996, Blackie Academic & Professional, New York, publisher page and Table of Contents.
Hess et al., "Oxidation of Linseed Oil—Temperature Effects," *Ind. Eng. Chem.* 1950, 42(7): 1424-1431.
Hevus et al., "Invertible Micellar Polymer Assemblies for Delivery of Poorly Water-Soluble Drugs," *Biomacromolecules*, 2012; 13(8):2537-2545.
Hofland, A., "Water-borne coatings for decorative and protective coatings: a comparative study," *Surface Coatings International*, 1994, 7:270-281.
Jansen at al., "Fast Monomers: Factors Affecting the Inherent Reactivity of Acrylate Monomers in Photoinitiated Acrylate Polymerization," *Macromolecules*, 2003, 36(11):3861-3873.
Johnson, R.W.; Fritz, E.E., "Fatty Acids in Industry," 1989, Marcel Dekker, Inc., New York, publisher page and Table of Contents.
Kabasakal et al., "Styrenation of Oils Based on Secondary Esters of Castor Oil," *J Coat. Technol.* Feb. 1995, 67(841):47-51.
Kazantsev et al., "Spontaneous polymerization of (meth)acrylamides in concentrated aqueous solutions," *Polymer*, Jul. 12, 2004, 45(15):5021-29.
Kelen et al., "Confidence intervals for copolymerization reactivity ratios determined by the Kelen-Tëdös method," *Polymer Bulletin*, Jan. 1980, 2(1):71-76.
Kohut et al., "Amphiphilic Invertible Polymers (AIPs) Micellization and Self-Assembly in Aqueous Solutions," *Amphiphiles: Molecular Assembly and Applications, ACS Symposium Series*, Sep. 19, 2011; Chapter 13, 1070:205-224.
Kudina et al., "PEG and Cholesterol-Containing Pyromellitates: Synthesis and Self-Assembly", *Macromolecular Chemistry and Physics*, Sep. 2013; 214(23):2761-2767.
Kudina et al., "Highly Efficient Phase Boundary Biocatalysis with Enzymogel Nanoparticles", *Angew. Chem Int. Ed. Engl.*, Jan. 7, 2014; Epub Nov. 8, 2013; 53(2):483-487.
Kudina et al., "Solvent-Responsive Self-Assembly of Amphiphilic Invertible Polymers Determined with SANS," *Langmuir*, Apr. 1, 2014; Epub Mar. 18, 2014; 30(12):3310-3318.
Kulkarni et al., Polymerizable monomers from castor oil. I. Vinyl monomers based on undecenoic acid, *J. Am. Oil Chemist's Soc.*, Jun. 1968; 45(6):465-467.
Lligadas et al., "Renewable polymeric materials from vegetable oils: a perspective," *Materials Today*, Sep. 2013, 16(9):337-343.

Lu et al., "Novel Polymeric Materials from Vegetable Oils and Vinyl Monomers: Preparation, Properties and Applications," *ChemSusChem.*, Feb. 17, 2009, 2(2):136-147.
Maiti et al., "RAFT polymerization of fatty acid containing monomers: controlled synthesis of polymers from renewable resources," *RSC Adv.*, 2013; 3:24983-90.
Mallegol et al., "Drier influence on the curing of linseed oil," *Prog. Org. Coat.* Nov. 2000, 39(2-4):107-113.
Meier et al., "Plant oil renewable resources as green alternatives in polymer science," *Chem. Soc. Rev.*, Nov. 2007, 36(11):1788-1802.
Montero de Espinosa and Meier, "Plant oils: The perfect renewable resource for polymer science?!" *European Polymer Journal*, May 2011, 47(5):837-852.
NDSU Research Foundation, "Acrylic Monomers Derived from Plant Oils—Synthesis and Use in High Value Polymers," Technology Case: RFT-462, 2 pages.
Neises and Steglich, "Simple Method for the Esterification of Carboxylic Acids," *Angew. Chem. Int. Ed. Engl.*, Jul. 1978, 17(7):522-524.
F.A. Norris, Extraction of fats and oils, in Bailey's Industrial Oil and Fat Products (Ed. Swern D.), Wiley, New York, 1996, publisher page and Table of Contents.
Odian, G. Principles of Polymerization, 1981, Wiley, New York, publisher page and Table of Contents.
Rodstrud et al., "Alkyd emulsions-properties and application. Results from comparative investigations of penetration and aging of alkyds, alkyd emulsions and acrylic disperions," *Surf Coat Int*, 1994, 1:7-16.
Roe et al., "Fatty acid amides. IV. Reaction of fats with ammonia and amines," *J Am Oil Chem Soc*, Jan. 1952, 29(1):18-22.
Scala et al., "Fatty Acid-Based Monomers as Styrene Replacements for Liquid Molding Resins," *Polymer*, Oct. 2004; 45:7729-7737.
Sharma et al., "Addition Polymers from Natural Oils—A Review," *Prog. Polym. Sci.*, Nov. 2006, 31(11):983-1008.
Solomon, D.H. The Chemistry of Organic Film Formers, 1971, Wiley, New York. , publisher page and Table of Contents.
Teeter, "Vinyl monomers derived from fats and oils," *J. Am. Oil Chemist's Soc.*, Apr. 1963; 40(4):143-156.
Tarnavchyk et al., "Reactive hydrogel networks for the fabrication of metal-polymer nanocomposites", *Macromolecular Rapid Communications*, 2009; 30(18):1564-9.
Tarnavchyk et al., "Synthesis and Free Radical Copolymerization of a New Vinyl Monomer from Soybean Oil," *ACS Sustainable Chem. Eng.*, Jun. 11, 2015, 1-14.
Varvarenko al., "Covalent grafting of polyacrylamide-based hydrogels to a polypropylene surface activated with functional polyperoxide", *Reactive and Functional Polymers*, Sep. 2010; 70(9):647-55.
Varvarenko et al., "Synthesis and colloidal properties of polyesters based on glutamic acids and glycols of different nature", *Chemistry and Chemical Technology*, 2013; 67(2):164-8.
Verhe, R.G. Industrial products from lipids and proteins, in *Renewable Bioresources: Scope and Modification for Non-Food Applications*, 2004, Stevens C.V.; Verhe R.G., John Wiley & Sons, Ltd, Chichester, publisher page and Table of Contents.
Williams et al., "Polymers from renewable resources: a perspective for a special issue of polymer reviews," *Polym. Rev.*, 2008, 48(1):1-10.
Wool, R.P.; Sun, X.S. *Bio-Based Polymers and Composites*, 2005, Elsevier, Amsterdam, publisher page and Table of Contents.
Yildiz et al., "Method for determining oxidation of vegetable oils by near-infrared spectroscopy," *J Am. Oil Chem. Soc.*, May 2001, 78(5):495-502.
Yuan et al., "Amidation of triglycerides by amino alcohols and their impact on plant oil-derived polymers," *Polym. Chem.*, Mar. 3, 2016, 7:2790-2798.

* cited by examiner

BIO-BASED ACRYLIC MONOMERS AND POLYMERS THEREOF

This application is a divisional application of U.S. patent application Ser. No. 15/502,342, filed on Feb. 7, 2017, now U.S. Pat. No. 10,315,985, which is the § 371 U.S. National Stage Application of International Application No. PCT/US2015/044288, filed Aug. 7, 2015, which claims the benefit of U.S. Provisional Application Ser. No. 62/035,114, filed Aug. 8, 2014, each of which is incorporated herein by reference in its entirety.

BACKGROUND

The US paint and coatings industry includes more than 1,000 companies with combined annual sales of about $22 billion and is expected to grow over the coming years. Polymer latexes are one of the most advanced polymeric materials produced for applications in coatings and paints. A unique process for producing polymer latexes with various properties is emulsion polymerization (free radical polymerization), which involves emulsification of monomers (or monomer mixtures) and their further polymerization resulting in the formation of latex particles from high molecular-weight polymers stabilized by surfactants in aqueous medium. This process is waterborne and does not involve any toxic or flammable solvents. Latex paints are considered much more environmentally friendly than conventional solvent borne systems.

The prominent polymer latexes for applications in paints and coatings are made from petroleum-based acrylic polymers or their combination with methacrylic polymers. They possess excellent properties, such as high weathering resistance, gloss, elasticity, chemical resistance, etc., but have some disadvantages, including small residues of unreacted monomers (causes unpleasant odor), reduced ability to form films and high cost.

Waterborne polymer latexes represent a significant portion of the paints and coatings market. For example, 70% of architectural paints sold in the United States are classified as waterborne paints. The second largest market for waterborne latexes is coatings that are applied on cars. Based on a 2011 BCC Research market report, the global market for waterborne coatings was $70 billion in 2012 and is expected to grow to $110 billion by 2017.

SUMMARY OF THE INVENTION

Triglycerides derived from plant oils and fats have proven difficult to convert into low molecular weight acrylic monomers. Currently, the production of fatty acrylates which are available on the market utilizes multistep synthetic procedures. For instance, the production of well-known fatty monomer-stearyl acrylate includes saponification, neutralization, reduction, acylation and other procedures which are quite expensive.

The invention provides a one-step method for converting a bio-based fatty acid ester, which can take the form of an oil, fat, wax, or other fatty acid ester, into acrylic monomers that can substitute for petroleum-based monomers in the production of acrylic polymers. This method can use essentially any plant oil, any animal fat, plant and animal waxes including insect waxes (provided the wax contains fatty acid esters), or other fatty esters as the raw material. While the invention is described, for convenience, primarily with respect to plant oil-derived fatty acid esters, particularly those derived from soybean oil, it should be understood that any bio-derived fatty acid ester can be utilized. The output of the synthetic method includes acrylic or (meth)acrylic fatty monomers that can be used directly in the production of latexes, plastics, thermoplastics, resins, adhesives, gels, surfactants, and other products that utilize acrylic polymers. Conveniently, the method does not require expensive equipment and can be performed in one step using a batch set-up designed for biodiesel production. It is not necessary to redesign existing equipment for polymerization or copolymerization, as the monomers can polymerize using existing bulk, solution or emulsion methods.

The method allows for the attachment of one acrylic/methacrylic group at the carbonyl of the fatty acyl group, while keeping all or most of the fatty double bonds in the fatty chain unaffected. The conjugated double bond of the acrylamide functional group is highly reactive in conventional addition free-radical polymerization which allows formation of linear polymers useful in industrial production of high volume polymer-based products including latex paints, adhesives, binders, plastics, etc. Advantageously, the non-conjugated (sometimes referred to herein as "isolated") double bonds in the fatty chain of the monomer (i.e., the fatty double bonds) remain mostly or entirely unaffected during free-radical polymerization of the monomer, resulting in polymers or copolymers having unsaturated fatty chains that allow for oxidative cross-linking and further tuning of the polymer performance.

The benefits of the invention may include a simple one step method for converting triglycerides into acrylic monomers; use of the bio-based monomers as a substitute for the petroleum-based monomers in a conventional synthesis, with little or no need to change the manufacturing process; and the presence of two types of double bonds (one conjugated and reactive, the other(s) non-conjugated and less reactive) at different locations within the acrylic monomers, which are not present in petroleum-based monomers. These fatty chain double bonds provide sites for cross-linking, thereby enabling production of polymers with enhanced functionality.

Thus, in one aspect, the invention provides a bio-based acrylic monomer that includes a bio-derived fatty acyl group comprising a carbonyl group; and an acrylic group; wherein the acrylic group is enterically linked, directly or indirectly, to the fatty carbonyl group. In one embodiment, the bio-based acrylic monomer that includes a bio-derived fatty acyl group comprising a carbonyl group; and an acrylamide group; wherein the acrylamide group is enterically linked, directly or indirectly, to the fatty carbonyl group.

In one embodiment, an exemplary bio-based acrylic monomer has formula (I):

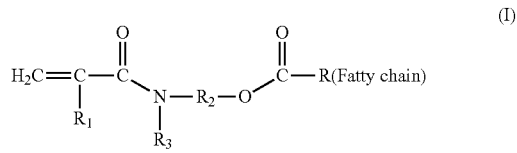

wherein R is a fatty chain derived from a plant oil or an animal fat;

$R_1$ and $R_3$ are each independently H, an aliphatic group, or an aromatic group; and $R_2$ is a divalent aliphatic group or aromatic group.

In one embodiment, the fatty chain R comprises a $C_5$-$C_{21}$ alkyl group or a $C_5$-$C_{21}$ alkenyl group. The fatty chain R may contain 0, 1, 2, 3, 4, 5 or 6 double bonds; preferably, R contains at least one double bond.

Exemplary plant oils from which the fatty chain R is derived include soybean oil, high oleic soybean oil, linseed oil, flaxseed oil, sunflower oil, safflower oil, canola oil, corn oil, cashew nut oil, olive oil, peanut oil, palm oil, sesame oil, cottonseed oil, rapeseed oil, walnut oil, almond oil, coconut oil, or any combination thereof. A preferred plaint oil is soybean oil. The fatty chain R can be derived from any convenient fatty acid, such as any of oleic, linoleic, linolenic, ricinoleic, myristoleic, palmitoleic, elaidic, euric, arachidonic, eleasteric, stearic, palmitic, arachidic, myristic, lauric, caprylic and capric acid, or mixtures thereof. In some embodiments of the bio-based monomer, the fatty chain R can include at least one functional group comprising an epoxy group, an acrylic group, or alcohol group.

In an exemplary embodiment, $R_1$ is H or a $(C_1-C_{10})$alkyl; $R_2$ is a $(C_1-C_{10})$alkylene, an alkylene glycol, or a polyalkylene glycol; and/or $R_3$ is H or a $(C_1-C_{10})$alkyl.

In another aspect, the invention includes a method for making the bio-based acrylic monomer. In one embodiment of the method, a bio-derived triglyceride, a hydroxy functional acrylic compound, such as a hydroxy functional acrylamide, and an optional catalyst are mixed, heated at a temperature between about 25° C.-60° C. for about 2-25 hours, and the resulting monomers are separated from the remaining components of the mixture. In another embodiment of the method, a bio-derived fatty ester, at least one of an acrylamide alcohol or an acrylamide ester, and an optional catalyst are mixed, heated at a temperature between about 25° C.-60° C. for about 2-25 hours, and the resulting monomers are separated from the remaining components of the mixture. Optionally, the mixture can include a cosolvent, for example in an amount of up to 50% wt.

In another aspect, the invention includes a polymer that includes at least one bio-based acrylic monomer of the invention. The polymer can be a homopolymer or a copolymer. In the case of a copolymer, the comonomer can be selected, without limitation, from an acrylate, such as an alkyl acrylate, a methacrylate, such as an alkyl methacrylate, an acrylamide, a methacrylamide, an acrylonitrile, or any combination thereof. Exemplary comonomers include 1,3-butadiene, a butyl acrylate, a butyl methacrylate, an ethyl acrylate, a hydroxyethyl acrylate, an isoprene, a maleic anhydride, a methyl acrylate, a methyl methacrylate, a 2-ethylhexyl methacrylate, a styrene, a vinyl acetate, a vinyl ether, a vinyl pyridine, a vinyl chloride, a poly(ethylene glycol) methacrylate, a poly(ethylene glycol) methyl ether methacrylate, a poly(ethylene glycol) methyl ether acrylate, a phenyl ether acrylate, and a polyfunctional vinyl monomer.

In another aspect, the invention includes the method for polymerization of a bio-based monomer, preferably a polymerization method involving free radical polymerization, and any polymer formed using the method of polymerization.

In another aspect, invention includes a latex that includes an emulsion that includes a polymer formed from a bio-based acrylic monomer of the invention.

In another aspect, the invention includes a waterborne coating that includes a polymer formed from a bio-based acrylic monomer of the invention.

In another aspect, the invention include a paint, adhesive, thermoplastic, plastic, resin, emulsion, surfactant, gel, coating or oil that includes a polymer formed from a bio-based acrylic monomer of the invention.

In another aspect, the invention include an article that includes a latex, waterborne coating, paint, adhesive, thermoplastic, plastic, resin, emulsion, surfactant, gel, coating, oil or polymer that includes a bio-based acrylic monomer of the invention. For example, a personal care product or industrial cleaning product may include a surfactant that includes a bio-based acrylic monomer of the invention.

Advantageously, the monomers can be used as a substitute for many different hydrophobic petroleum-based monomers in common free-radical or ionic polymerization techniques. Industrial applications include use of the monomers in the production of polymeric emulsions (e.g. latexes), plastics, thermoplastics, resins, adhesives, gels, chemical binders, surfactants, coatings, and paints.

DETAILED DESCRIPTION OF ILLUSTRATIVE EMBODIMENTS

Figure 1:
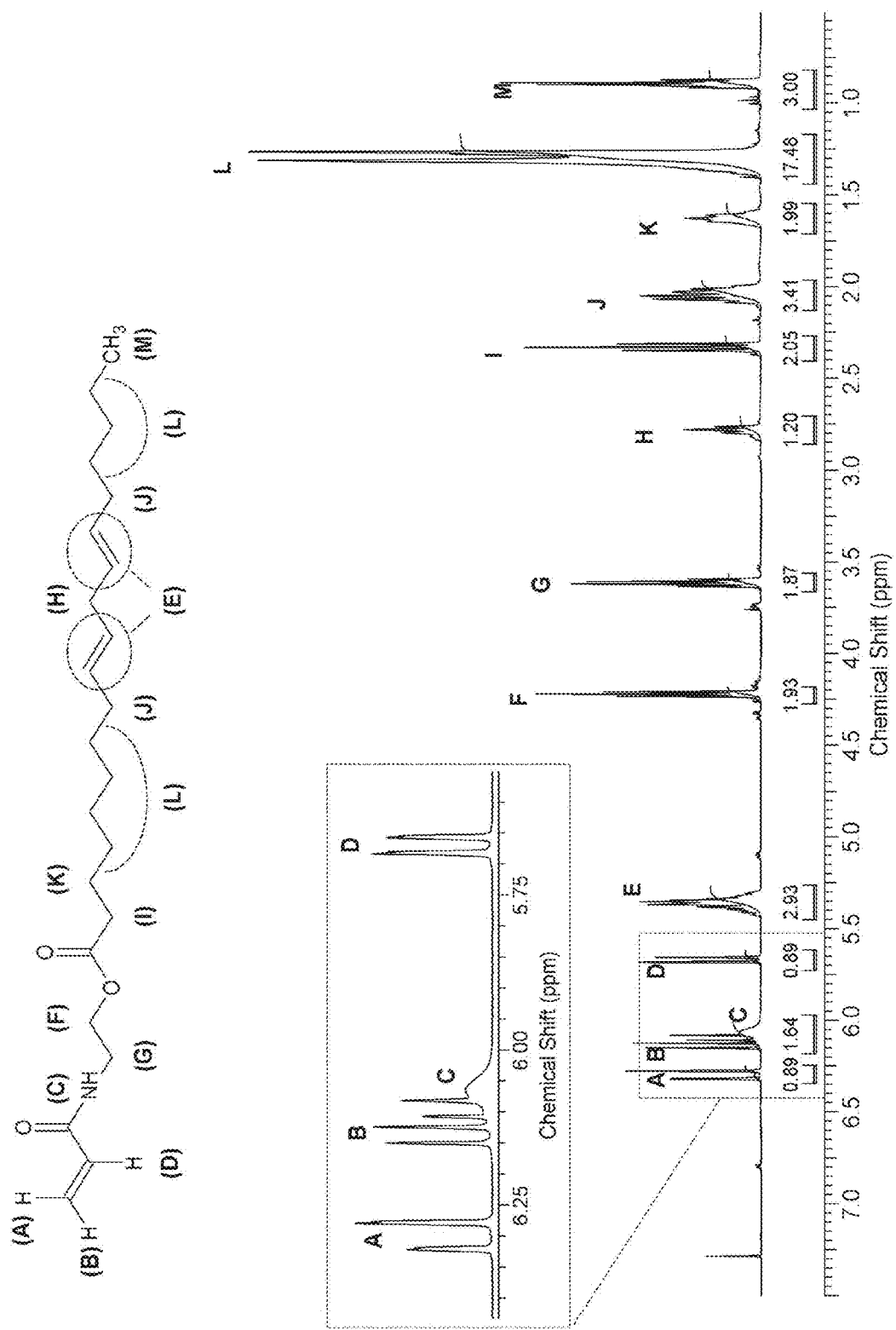
FIG. 1 shows a proton ($^1$H) NMR spectrum of a representative soybean oil based monomer (SBM).

The invention provides a new bio-based acrylic monomer, particularly a plant oil-based acrylic monomer, which is well-suited for free radical polymerization (also known as emulsion polymerization) and latex formation in aqueous medium. The invention sets forth a one-step method for converting naturally occurring triglycerides or other fatty acid esters into acrylic monomers that can advantageously substitute for petroleum-based monomers in the production of acrylic polymers. Attachment of an acrylic group to the carbonyl of the fatty acyl, in contrast to attachment of the acrylic group to the double bonds in the unsaturated fatty chain, allows for the synthesis of acrylic fatty acid-based monomers that grow as linear addition polymers. Exemplary starting materials include, without limitation, naturally occurring, non-naturally occurring and/or (semi)synthetic triglycerides or other fatty acid esters, or any combination thereof.

As used herein, the term "fatty acid ester(s)" includes but is not limited to esters of fatty acids containing more than five, preferably more than eight carbon atoms. An exemplary fatty acid ester can be derived from synthetic (non-naturally occurring), (semi)synthetic, or naturally occurring saturated or unsaturated fatty acids, including their isomers, and mixtures of such esters. A (semi)synthetic compound is understood to be a compound produced by chemical alteration of a naturally occurring starting material.

The synthetic method is exemplified with triglycerides and fatty alkyl esters (e.g., biodiesel) as the fatty acid source, since they are readily available, renewable and relatively inexpensive; but essentially any natural or (semi)synthetic source of fatty acid esters is suitable for use as the raw material, including plant oil, animal fat, biodiesel or bio-derived fatty waste, to produce the bio-based monomer. By incorporating bio-derived saturated and unsaturated fatty acids from selected plant and animal sources, these monomers offer unique functionality due to the position, number and nature of internal double bonds, thereby providing sites for cross-linking and the ability to tune performance by affecting properties such as glass transition temperature, hardness, autooxidation, surface activity, solvent resistance and impact strength.

The acrylamide and (meth)acrylamide functionality has the added advantage of a localization of electron density near the nitrogen atom which facilitates the formation of higher molecular weight (i.e., longer) linear polymers during free radical polymerization (compared to other vinyl polymers), yielding polymers that can have molecular weights (MW) of greater than 40,000 g/mol, 60,000 g/mol or higher.

The plant oil-based monomer of the invention is exemplified, without limitation, by a soybean oil-based monomer (referred to herein as an SBM). Soybean oil is considered one of the most abundant and cheapest renewable materials available in large quantities, and has the ability to form resins due to autooxidation and subsequent cross-linking. To the best of our knowledge, there is no open literature report on the preparation, properties and utilization of soybean oil-based (meth)acrylamide functionalized fatty esters as monomers for free radical polymerization. Additionally, no latexes are reported from such soybean oil-based acrylic monomers as a single component in emulsion polymerization, or in combination with acrylic monomers to produce acrylic latexes. Replacing all or part of the petroleum-based acrylic components in the latex with a natural ingredient will be beneficial for the broad variety of polymeric materials, wherever paints, coatings, adhesives, plastics, thermoplastics, gels, surfactants etc., are used. The invention accordingly encompasses those materials into which one or more bio-based monomers of the invention are incorporated.

While soybean oil-based monomers are described herein as an exemplary embodiment of the invention, it should be understood that for all embodiments described with reference to soybean oil-based monomers, the invention encompasses and equally applies to analogous monomers that are made from other plant oils, animal fats, etc. Additionally, while the exemplified soybean oil monomer in the examples is acrylamide or (meth)acrylamide monomer, the plant and animal oils can be incorporated into other acrylic monomers, including other substituted acrylamide monomers.

Exemplary Bio-Based Acrylic Monomers

An exemplary bio-based monomer of the invention is an acrylic monomer (I):

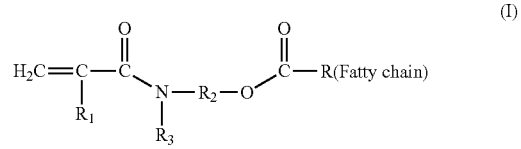

R is fatty chain, preferably derived from a plant oil or an animal fat; preferably R is a $C_5$-$C_{21}$ aliphatic group, preferably a $C_5$-$C_{21}$ alkyl group or a $C_5$-$C_{21}$ alkenyl group, more preferably a linear $C_5$-$C_{21}$ alkyl group or a linear $C_5$-$C_{21}$ alkenyl group. A preferred aliphatic group is a $C_8$-$C_{21}$ aliphatic group. The aliphatic group preferably includes a linear chain of 5, 6, 7, 8, 9, 10, 11, 12, 13, 14, 15, 16, 17, 18, 19, 20, 21, 22 or more carbon atoms, and may contain 0 (saturated), 1 (monounsaturated), 2, 3, 4, 5, or more double bonds; the aliphatic group may include one or more functional groups such as hydroxyl, methyl, methoxy, epoxy or carbonyl; preferably, the fatty chain is derived from a plant oil, such as a vegetable or a nut oil; more preferably, it is derived from plant fatty acids found in soybeans, including stearic acid, oleic acid, palmitic, linoleic acid or linolenic acid.

$R_1$ is H, an aliphatic group, or an aromatic group, such as an alkyl group, an aryl group, an alkoxy group, an alkaryl group, an aryloxy group, an ether, or an amide; preferably $R_1$ is H or an alkyl group; in an exemplary embodiment $R_1$ is H or a ($C_1$-$C_{10}$)alkyl such as methyl, ethyl, propyl, isopropyl, butyl, isobutyl and the like; $R_1$ can be saturated or unsaturated; linear, branched, cyclic or heterocyclic; substituted or unsubstituted; $R_1$ is preferably H or methyl.

$R_2$ is a divalent aliphatic group or aromatic group, such as an alkylene group, an arylene group, an alkoxy group, an alkaryl group, an aryloxy group, an ether, or an amide; preferably $R_2$ is an alkylene group; in an exemplary embodiment $R_2$ is a ($C_1$-$C_{10}$)alkylene such as methylene, ethylene, propylene, isopropylene, butylene, isobutylene and the like; $R_2$ can be saturated or unsaturated; linear, branched, cyclic or heterocyclic; substituted or unsubstituted; in an exemplary embodiment wherein $R_2$ is an ether, $R_2$ is an alkylene glycol fragment, such as an ethylene glycol fragment (—$CH_2$—$CH_2$—O—$CH_2$—$CH_2$—), or a polyalkylene glycol fragment, such as a polyethylene glycol fragment (—[$CH_2$—$CH_2$—O]$_n$—$CH_2$—$CH_2$—, where n=1 to 50, preferably n=1, 2, 3, 4, 5, 6, 7, 8, 9 or 10).

$R_3$ is H, an aliphatic group, or an aromatic group, such as an alkyl group, an aryl group, an alkoxy group, an alkaryl group, an aryloxy group, an ether, or an amide; preferably $R_3$ is H or an alkyl group; in an exemplary embodiment $R_3$ is H or a ($C_1$-$C_{10}$)alkyl such as methyl, ethyl, propyl, isopropyl, butyl, isobutyl and the like; $R_3$ can be saturated or unsaturated; linear, branched, cyclic or heterocyclic; substituted or unsubstituted.

In some embodiments, $R_1$ is covalently linked to $R_2$ such that $R_1$ and $R_2$ may be taken together with optional intervening atoms to form one or more optionally substituted rings optionally containing one or more heteroatoms; in some embodiments, $R_1$ is covalently linked to N or $R_3$ such that $R_1$ and either N or $R_3$ may be taken together with optional intervening atoms to form one or more optionally substituted rings optionally containing one or more heteroatoms.

In some embodiments, one or both hydrogen atoms at the terminal $CH_2$ of the vinyl group (i.e., at position C1 of the monomer) are independently substituted with an amide or nitryl.

As used herein, the term "aliphatic" or "aliphatic group" means a saturated or unsaturated linear (i.e., straight chain), cyclic, or branched hydrocarbon group. This term is used to encompass alkyl (e.g., —CH$_3$) (or alkylene if within a chain such as —CH$_2$—), alkenyl (or alkenylene if within a chain), and alkynyl (or alkynylene if within a chain) groups, for example. The term "alkyl group" means a saturated linear or branched hydrocarbon group including, for example, methyl, ethyl, n-propyl, isopropyl, butyl, isobutyl, tert-butyl, amyl, heptyl, dodecyl, octadecyl, amyl, 2-ethylhexyl, and the like. The term "alkenyl group" means an unsaturated, linear or branched hydrocarbon group with one or more olefinically unsaturated groups (i.e., carbon-carbon double bonds), such as a vinyl group. The term "alkynyl group" means an unsaturated, linear or branched hydrocarbon group with one or more carbon-carbon triple bonds. The term "cyclic group" means a closed ring hydrocarbon group that is classified as an alicyclic group, aromatic group, or heterocyclic group. The term "alicyclic group" means a cyclic hydrocarbon group having properties resembling those of aliphatic groups. The term "aromatic group" or "aryl group" means a mono- or polynuclear aromatic hydrocarbon group. The term "heterocyclic group" means a closed ring hydrocarbon in which one or more of the atoms in the ring is a heteroatom, i.e., element other than carbon (e.g., nitrogen, oxygen, sulfur, etc.).

In some embodiments of the monomer of the invention, the fatty chain R group can be activated at the site of one or more double bonds, e.g., by epoxidation, acrylation, or by the incorporation of alcohol groups. Briefly, incorporation of acrylate groups or alcohol groups typically first involves the generation of an epoxide intermediate. The double bonds can be derivatized using epoxidation, Diels-Alder chemistry, or thiol-ene chemistry. Derivatives such as epoxy-functional, acrylate-functional and alcohol-functional (polyol) polymers are likewise included in the invention. The fatty chain R group can be activated either before or after the transesterification reaction (or both before and after).

In exemplary embodiments, R is a fatty chain derived from a plant oil such as soybean oil, R$_1$ is H or methyl, and R$_2$ is C$_1$-C$_6$ linear or branched alkyl, such as methyl, ethyl, propyl, isopropyl, butyl, isobutyl, pentyl, hexyl, etc., and R$_3$ is H. Exemplary embodiments include (acryloylamino)alkyl or (2-methylacryloylamino)alkyl esters of fatty acids derived from a plant oil such as soybean oil, as described in the examples below.

One non-limiting exemplary monomer of the invention is:

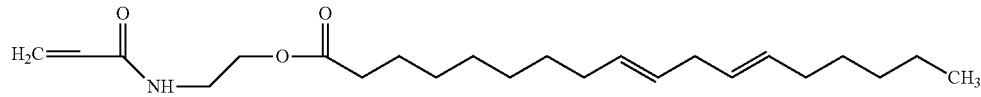 [SMILES: C=CC(=O)NCCOC(=O)CCCCCCC/C=C/C/C=C/CCCCC]

More generally, the fatty chain R can be derived from any biological material, such as a plant oil or an animal fat, including a (semi)synthetic or naturally occurring saturated or unsaturated fatty acid. Suitable preferred unsaturated fatty acids include oleic, linoleic, linolenic, ricinoleic, myristoleic, palmitoleic, elaidic, euric, arachidonic, eleasteric acids. Suitable preferred saturated fatty acids include stearic, palmitic, arachidic, myristic, lauric, caprylic and capric. Suitable fatty acids may include medium chain fatty acids (6 to 12 carbon atoms) (MCFA), long chain fatty acids (13 to 22 carbon atoms) (LCFA) and very long chain fatty acids (23 or more carbon atoms) (VLCFA). Suitable naturally occurring plant and animal fatty acids also include those that are hydroxylated or otherwise oxygenated, such as hydroxy fatty acids that contain one or more secondary hydroxyl groups, exemplified by 2-hydroxy docosanoic acid, 15-hydroxy hexadecanoic acid, and ricinoleic acid (from castor oil). Additional suitable naturally occurring plant and animal fatty acids include epoxy and furanoid fatty acids, keto (oxo) fatty acids and methoxy fatty acids. Fatty acids derived from plant oils, in particular, soybean oil, rapeseed oil, flaxseed oil (linseed oil), canola oil, corn oil, sunflower oil, cottonseed oil, palm oil, castor oil, and mixtures thereof, are especially preferred for use herein.

More generally, the plant oil can be any vegetable oil or a nut oil, or mixture thereof. Exemplary plant oils include, but are not limited to, vegetable oils such as soybean oil (including high oleic soybean oil), flaxseed oil (linseed oil), rapeseed oil, sunflower oil, safflower oil, canola oil, corn oil, olive oil, peanut oil, palm oil, sesame oil, cottonseed oil, coconut oil, castor oil, and nut oils such as cashew nut oil, walnut oil, and almond oil. The plant oil can be of a traditional variety or it can be a high oleic oil, such as high oleic soybean oil, Soybean oil in general is highly suitable due to its low cost and availability. Hydrogenated or partially hydrogenated plant oils can also be used.

Monomer Synthesis

The invention provides a method for synthesizing biobased acrylic monomers that involves a transesterification reaction between a plant oil or animal fat, and an acrylamide-containing alcohol (i.e., a hydroxyl functional acrylamide) or ester. The reaction is a one-step method that converts a plant oil or animal fat into a reactive acrylic fatty acid-based monomer. In one embodiment, the process involves (1) mixing of oil or fat and a hydroxy functional acrylamide with base catalyst and an optional cosolvent (2) heating the components at a temperature between about 25° C. and 60° C. for about 2-25 hours, and (3) separating the product monomers. The temperature at which the reaction is performed can be between 20° C. and 80° C. Typically the hydroxy functional acrylamide is provided in excess over the number of moles of fatty acid; for example, it may be provided at a level of 2.0 to 2.5 in molar excess over the number of moles of fatty acid.

As a base catalyst for this reaction, inorganic bases such as sodium hydroxide, potassium hydroxide, metal alkoxides including sodium methoxide, and sodium ethoxide, as well as organic nucleophilic additives, such as triethylamine and pyridine, can be used. Transesterification may likewise proceed under acidic catalytic conditions as well, particularly in presence of Lewis or Bronsted acids. The following groups of catalysts which include homo- and heterogeneous catalysts can be used: inorganic tin catalysts (such as Sn(Oct)$_2$, SnCl$_2$, SnO, etc.); organotin catalysts (such as dibutyltin dilaurate, dibutyltin oxide, etc); sulfuric acid and sulphonic acid catalysts; bismuth-based catalysts; zinc-based catalysts, etc.

As a cosolvent, tetrahydrofuran, dioxane, acetone, butanone, ethylene carbonate, propylene carbonate, methyl isobutyl ketone, cyclohexanone, water, dimethylformamide dimethyl sulfoxide or other solvent can be used. A preferred solvent is one that will not participate in the reaction; for example, a preferred solvent does not contain an ester group, an alcohol group, or other reactive group. Moderately polar or amphiphilic solvents are preferred, since one reactant is relatively polar and hydrophilic (the acrylamide alcohol) and the other is relatively nonpolar and hydrophobic (the fatty acid). For example, although water can be used as a cosolvent, it may be too polar to serve well in this capacity; likewise, if hexane is used, although it is inert with the respect to the reaction, it may be too nonpolar. The presence of cosolvent up to 50% wt. facilitates reaction; however, the synthesis can be performed without cosolvent as well or in the presence of non-ionic and/or ionic surfactant (soap) such as potassium stearate, sodium stearate, other alkali metal salts of fatty acids; additionally or alternatively, a surfactant can be generated in situ during reaction. The method is applicable to any type of plant oils and animal fats.

The reaction mixture may also include one or more stabilizers, such as free radical scavengers. The optional free radical scavenger helps prevent the unintended initiation of polymerization. Exemplary free radical scavengers include, without limitation, dibutylhydroxytoluene and ionol.

In an exemplary embodiment, fatty acrylamide or methacrylamide monomers (e.g., (acryloylamino)alkyl or (2-methylacryloylamino)alkyl esters of fatty acids) are made using a transesterification reaction of plant oil with acrylamide- or methacrylamide-containing alcohols (e.g., N-(hydroxyalkyl)acrylamide or N-(hydroxyalkyl)methacrylamide), according to the method described herein. As readily available embodiments of N-(hydroxyalkyl) acrylamide and N-(hydroxyalkyl)methacrylamide, respectively, the hydroxyethyl compounds N-(2-hydroxyethyl)acrylamide and N-(2-hydroxyethyl)methacrylamide are exemplary starting materials, although it should be understood that their hydroxymethyl, hydroxypropyl, hydroxybutyl, hydroxyisopropyl or hydroxyisobutyl counterparts can be used as well.

The resulting fatty acrylamide (or methacrylamide) monomers can be used as fatty acid based acrylic monomers in synthesis of addition polymers, similar to conventional acrylic monomers that are broadly used for commercial production of a variety of polymers.

Exemplary synthetic schemes are as follows:

(a) acrylamide alcohol, i.e., N-(2-hydroxyethyl)acrylamide+triglyceride:

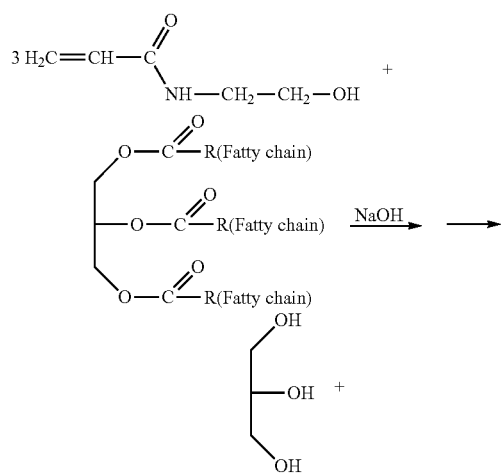

-continued

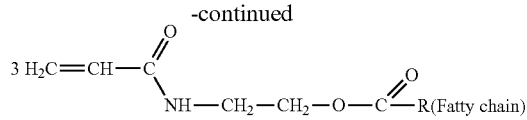

(b) acrylamide alcohol or acrylamide ester+fatty alkyl ester:

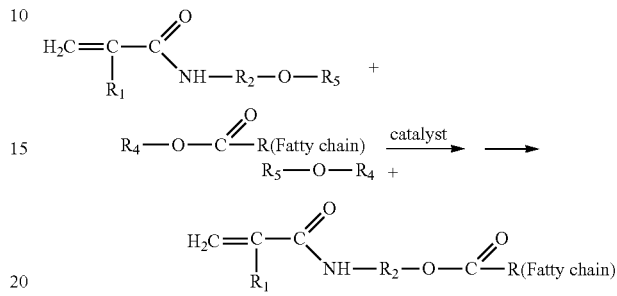

wherein $R_1$ and $R_2$ are as above for compound (I); $R_5$ is H (for the alcohol), or an acyl group (for the ester), for example acetyl —C(O)—CH$_3$; and $R_4$ is a H, alkyl, or a primary, secondary, or tertiary alcohol, or fragment thereof, such as —CH$_2$OH, —CH$_2$CH$_2$OH, glyceryl alcohol, or glyceride fragment, and the like.

The present invention utilizes acrylamide alcohols and acrylamide esters as starting materials for transesterification of plant oils, which compounds are preferred as starting materials over hydroxy acrylates. Hydroxy acrylates (esters) are inexpensive, but the end result of the transesterification reaction with hydroxy acrylates is a heterogeneous mix of diesters including bifunctional acrylates (cross-linkers) and disoyates (e.g., where soybean oil is the plant oil) at equilibrium quantities. The crosslinking compounds, e.g., diacrylates, are difficult to separate and can interfere with linear polymerization. An advantage of acrylamide alcohols is that the amide group is inert in the transesterification process, thereby allowing the alcohol group to react with the plant oil and substitute glycerol, for example, in the case of a triglyceride reactant, without cross-reaction.

It will be appreciated that when a plant or animal fat or oil is used as a starting material, the result will be a heterogeneous mixture of monomers due to the heterogeneity of fatty acids present in the original biomaterial. Even at the molecular level, a plant or animal triglyceride may contain up to three distinct fatty acids, so the monomers that result from the synthetic method of the invention will likewise be heterogeneous, each containing only one of the multiplicity of fatty acids that may be naturally present in the plant or animal fat or oil.

Polymers and Polymerization

The invention involves not only the synthesis of novel bio-based (e.g., soybean oil-based) acrylic monomers, but also their use in free radical polymerization and copolymerization. The invention thus further includes a method for utilizing the novel bio-based acrylic monomer in any polymerization reaction including, but not limited to, free radical polymerization, as well as the resulting polymers. Polymers incorporating the novel bio-based acrylic monomer can be homopolymers or copolymers. The term "polymer" is inclusive of both homopolymers and copolymers. The term "copolymer" includes, without limitation, alternating or periodic copolymers, statistical or random copolymers, terpolymers, star polymers, block copolymers such as diblock or tri block copolymers, and graft copolymers. A copolymer may be linear or branched. Suitable comonomers for copolymerization with the novel bio-based acrylic monomer of the invention include, for example, any vinyl monomer. An exemplary vinyl comonomer is shown below, wherein R is any organic group of interest.

Exemplary comonomers which have significant industrial value and which can be copolymerized with the monomers of the invention include acrylic acid, acrylonitrile, acrylamide, 1,3-butadiene, butyl acrylate, butyl methacrylate, ethyl acrylate, hydroxyethyl acrylate, isoprene, maleic anhydride, methacrylamide, methacrylic acid, methacrylate, methyl acrylate, methyl methacrylate, 2-ethylhexyl methacrylate, styrene, vinyl acetate, vinyl ethers, vinyl pyridine, vinyl chloride; other alkyl acrylates, alkyl meth(acrylates), and ethylene glycol derivatives such as, for example, poly(ethylene glycol) methacrylate (various molecular weight), poly (ethylene glycol) methyl ether methacrylate (various molecular weight), poly(ethylene glycol) methyl ether acrylate (various molecular weight), phenyl ether acrylate, and bi-, tri-, tetra- and polyfunctional vinyl monomers (crosslinkers) such as divinylbenzene and ethylene glycol diacrylate, including oligomeric and polymeric acrylated/methacrylated or polyacrylated/methacrylated compounds, as well as derivatives of these various monomers. More generally, any suitable acrylic or vinyl monomer can be employed as a comonomer.

The bio-based acrylic monomer of the invention is reactive and well-suited for emulsion polymerization and latex formation in aqueous medium for further applications in, for example, coatings and paints. Emulsion polymerization (free radical polymerization) can be employed to form polymer latexes, either from the bio-based acrylic monomer, such as soybean oil-based monomer (SBM) as a single ingredient, or from the bio-based acrylic monomer in combination (e.g., via copolymerization) with commercially available vinyl monomers (including, without limitation, acrylates (e.g., butylacrylate), methacrylates (e.g., methyl methacrylate, 2-ethylhexyl methacrylate), styrene, acrylonitrile, 1,3-butadiene; bi-, tri-, tetra- and polyfunctional vinyl compounds, for instance, divinylbenzene, ethylene glycol diacrylate, polyacrylated/methacrylated compounds, etc., which are widely used in industry for manufacturing latexes for paints and coatings.

Polymerization of Bio-Based Acrylic Monomers

Bio-based acrylic monomers can be polymerized and copolymerized via common free-radical or ionic, in particular anionic, polymerization techniques. Examples of techniques that can be used include, without limitation, free-radical polymerization techniques including atom transfer radical polymerization (ATRP), reversible addition-fragmentation chain transfer polymerization (RAFT), and stable free radical polymerization (SFRP).

The polymerization pathway of the soy-based monomer in free radical polymerization was found to lead to the formation of linear soybean-based polymers and copolymers, which principally distinguishes the polymerization behavior of the soy-based monomers of the invention from other soy-based acrylates reported in literature. The acrylic monomer of the invention is conjugated and therefore readily polymerizes, as distinguished from soy-based vinyl ethers. Known methods for synthesizing fatty acid based monomers include various acylation reactions (see U.S. Pat. No. 8,450,414 B2; US 2008/0183000 A1). However, until now acrylic fatty acid based monomers have not been synthesized using direct transesterification of plant oil with acrylamide- or methacrylamide-containing alcohols, as described herein. Without intending to be bound by theory, it is believed that attachment of the acrylic species to the fatty carbonyl group, in contrast to attachment to the double bonds of unsaturated fatty acids or plant oils, yields acrylic fatty acid based monomers capable of growing linear addition polymers.

Advantageously, the isolated (non-conjugated) double bonds in the fatty acid of the constituent monomer remain unaffected by the linear, free radical polymerization that occurs through the conjugated acrylic double bond. The amount of double bond remaining in the polymer or constituent monomer can be determined by any convenient method. For example, the amount of double bond in the monomer or polymer can be determined using nuclear magnetic resonance spectroscopy (NMR). A typical value for the number of double bonds in a polymer of the invention (prior to cross-linking or derivatization) will depend on the biological source of the fatty acid, but may range from 0 to 3.0 mole of double bonds per mole of fatty acid, more preferably about 1.0 to about 2.0 mole of double bonds per mole of fatty acid. The percentage of the original fatty double bonds that remain unaffected in the monomer or polymer of the invention can be over 80%, over 85%, over 90%, or over 95%, for example.

Advantageously, the monomers of the invention may substitute for hydrophobic petroleum-based acrylates and methacrylates in the market. Exemplary applications include synthesis of polymeric emulsions (latexes), plastics, thermoplastics, resins, adhesives, gels, surfactants and the like. It is expected that the monomers of the invention will allow extension of the application of renewable resources to substitute for petroleum-based chemicals in many areas and industries. An important application of the new soybean oil-based polymer latexes is expected to be within the very large and profitable market of coatings and paints. The natural soybean oil-based monomer is expected to be a good substitute for petroleum based hydrophobic monomers such as ethylhexyl acrylate and ethylhexyl methacrylate which are the base ingredients of latex paints (their content may reach up to 70 wt. %). Also, incorporation of new soy-based acrylic monomer into latex will improve the self-crosslinking ability of the new coatings, as well as such physicochemical properties such as film formation and hydrophobicity, and make the coatings environmentally friendly. Moreover, using renewable feedstock will also have an economic impact on the manufacturing of coatings and paints. Using SBM, stable latexes can be formed under ambient conditions that can be easily applied using conventional equipment for making coatings (for example, casting). Besides physico-chemical advantages, no volatile organic residues, and reduced odor and flammability, the new latexes will be environmental friendly because of the natural soybean ingredient.

The monomers of the invention find application in a number of diverse industrial settings. A broad variety of renewable soybean-based polymeric materials (not only latexes) can be developed utilizing the bio-based acrylic monomers of the invention. Besides the application in latex formation and manufacturing of waterborne coatings, SBM is useful for designing a variety of renewable soybean-based polymers, in particular, polymer thermoplastics, surfactants in personal care applications and adhesives.

Thermoplastics account for more than 70% of all polymers produced. The thermoplastic industry is expected to grow by 4.9% over the next five years and reach an estimated $8.2 billion by 2017. Plant-based polymer thermoplastics are attractive alternatives for partially replacing conventional acrylonitrile butadiene styrene (ABS), polypropylene, polyethylene etc.

The US personal care retail market is valued at over $70 billion. The segment defined as natural products in hair, skin, and cosmetics is valued at $7 billion. The quantity of surfactants used in this segment amounts to almost 800 million pounds. Surfactants constitute approximately 15% of the raw material costs of personal care products.

There is in addition a forecast of almost $50 billion for the global adhesives market in 2019. Acrylic-based (potential replacement by SBM-based) adhesives are the largest consumed product. They accounted for 35.4% of the total adhesives consumed in 2012.

In some embodiments, the invention may offer one or more of the following advantages or benefits: it provides a one-step method of converting triglycerides into acrylic monomers; the novel bio-based acrylic monomers can be used directly as a substitute for some or all of the petroleum-based monomers in a conventional synthesis, with no need to change the manufacturing process; and/or preservation of double bonds in bio-derived fatty chains, which are not present in petroleum-based monomers, and which provide useful sites for cross-linking, thereby enabling production of polymers with enhanced functionality.

The term "comprises" and variations thereof do not have a limiting meaning where these terms appear in the description and claims.

As used herein, "a," "an," "the," "at least one," and "one or more" are used interchangeably.

As used herein, the term "or" is generally employed in the sense as including "and/or" unless the context of the usage clearly indicates otherwise.

Also herein, the recitations of numerical ranges by endpoints include all numbers subsumed within that range (e.g., 1 to 5 includes 1, 1.5, 2, 2.75, 3, 3.80, 4, 5, etc.).

The examples that follow more particularly exemplify illustrative embodiments. In several places throughout the application, guidance is provided through lists of examples, which examples can be used in various combinations. In each instance, the recited list serves only as a representative group and should not be interpreted as an exclusive list.

EXAMPLES

The present invention is illustrated by the following examples. It is to be understood that the particular examples, materials, amounts, and procedures are to be interpreted broadly in accordance with the scope and spirit of the invention as set forth herein.

The examples illustrate an approach for synthesizing an exemplary bio-based acrylic monomer, soybean oil-based monomer (SBM) and utilizing it in a free radical polymerization. The SBM polymer obtained was successfully separated, purified and characterized. Utilizing this approach at its current efficiency, 1.05 pounds of SBM can be made from every pound of soybean oil. The new SBM can be copolymerized with a range of commercially available vinyl comonomers, such as, without limitation, acrylates, methacrylates, butylacrylates, methyl methacrylates, 2-ethylhexyl methacrylates, and/or vinyl acetate and styrene, for synthesis of polymer latexes from the SBM.

Example I

Synthesis of a Novel Soy-Based Monomer Suitable for Free Radical Polymerization

Acrylic monomers are valuable reagents in chemical industry, particularly in polymer-related manufacturing. Different acrylation reactions have been developed to synthesize fatty acid based acrylic monomers. Acrylic species can be attached to the fatty carbonyl group. Attachment of acrylic group to the fatty carbonyl, in contrast to the attachment to the double bonds, allows for the synthesis of acrylic fatty acid based monomers capable of growing linear addition polymers.

Soy-Based Monomer Synthesis

Acrylic soybean oil-based monomers were synthesized using transesterification of soybean oil with acrylamide- or methacrylamide-containing alcohols. The synthetic procedure to produce the exemplary new soy-based monomer (SBM) suitable for use in free radical polymerization is a one-step synthesis directly from soybean oil.

A two-neck, 500 ml round bottom flask equipped with mechanical stirrer was charged with 115 g of N-hydroxyethyl-acrylamide, 150 g of soybean oil, 150 ml of tetrahydrofuran and 0.1 g of 2,6-dimethylphenol. The reaction mixture was heated up to 40° C. and 1.5 g of ground sodium hydroxide was added slowly at continuous stirring. The reaction mixture was stirred at 40° C. until complete homogenization (approx. 3 hours), and allowed to stay overnight at room temperature. Later the content of the reaction flask was mixed with 100 ml of methylene chloride in a separation funnel. Then the liquid was washed 4 times with 5% brine and separated by centrifugation. The aqueous layer was discarded and the organic layer was dried over magnesium sulphate and filtered. The volatile methylene chloride was removed by distillation at reduced pressure giving 180 g of SBM. SBM is stabilized with 0.05-0.15 g of 2,6-Di-tert-butyl-4-methylphenol.

The resulting SBM contains one acrylic double bond linked to one fatty chain which varies between fully saturated, mono- and poly-unsaturated, depending on soybean oil composition.

In the case of transesterification of commodity soybean oil, a representative SBM is (acryloylamino)ethyl linoleate:

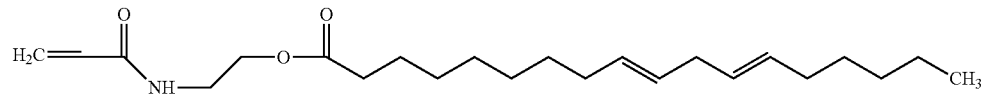 [SMILES: C=CC(=O)NCCOC(=O)CCCCCCC/C=C/C/C=C/CCCCC]

The structure of the synthesized monomer was confirmed using ¹H NMR spectroscopy (FIG. 1) by the presence of the characteristic peaks of the protons of the acrylic double bond at 6-6.6 ppm, the peaks of the protons of the ethylene linkage between the amide and ester groups at 3.6 and 4.20 ppm, and signals from the fatty acid chains (0.8 to 2.8 ppm). ¹H NMR (CDCl₃, 400 MHz): δ 0.87 t (3H, CH₃); 1.26 (16-18H, (CH₂)₃₋₉); 1.61 (2H, C(O)—CH₂—CH); 2.10 (3-4H, CH₂—CH₂—CH=); 2.33 dt (2H, C(O)—CH₂—CH₂); 2.77 (2H, =CH—CH₂—CH=); 3.6 (2H, NH—CH₂); 4.2 (2H, CH₂—O—); 5.35 (2-3H, CH=CH); 5.66 (1H, CH₂=CH—C(O)); 6.12 (1H, HCH=CH—C(O)); 6.3 (1H, HCH=CH—C(O)).

Figure 2:
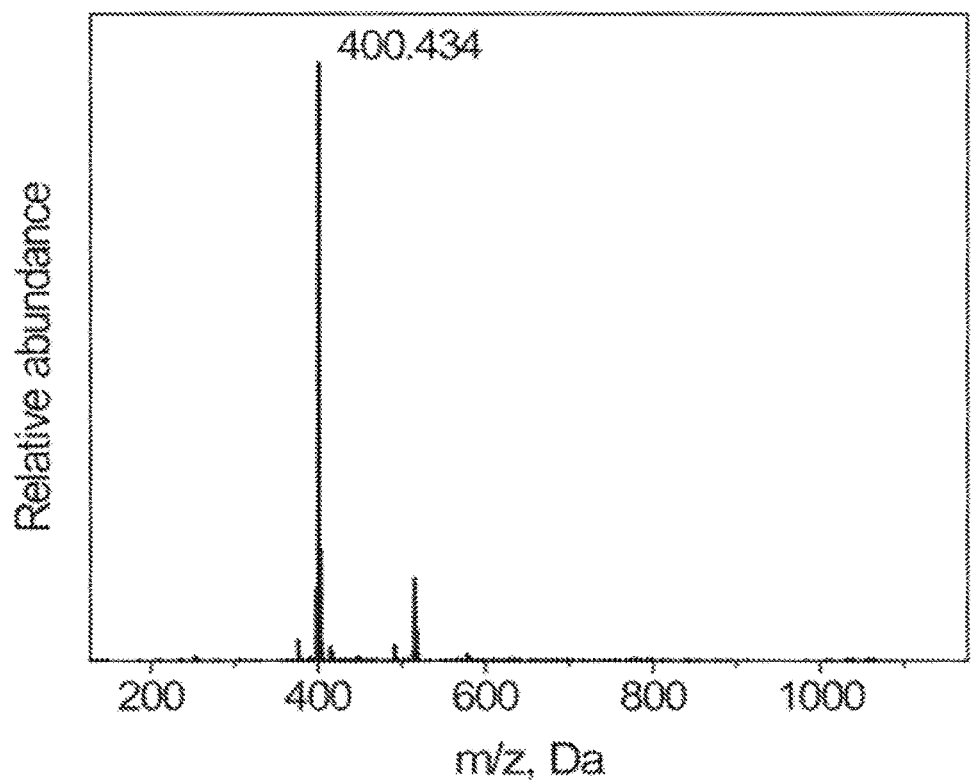
FIG. 2 shows a mass spectrum of a representative soybean oil based monomer (SBM).

The molecular weight of the SBA monomer was determined using mass-spectrometry (FIG. 2). After deducing the molecular weight of a sodium atom, it is a perfect match (377) with the theoretical average SBA molecular weight (375). Mass signals of SBM belong to polymerizable molecules containing N-acryloyl fragment in the chemical structure.

Figure 3:
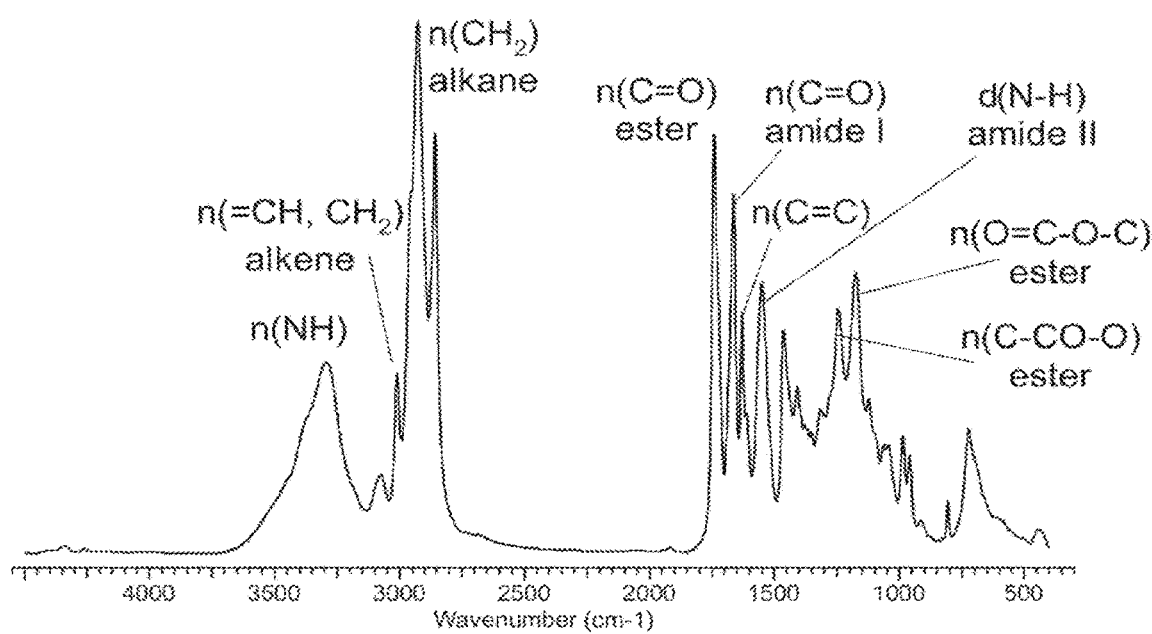
FIG. 3 shows a FT-IR spectrum of a representative soybean oil based monomer (SBM).

Using FT-IR spectroscopy it is concluded that the appearance of the strong NH adsorption band at 3200-3400 cm⁻¹, the carbonyl (amide I) band at 1670 and the NH (amide II) band at 1540 cm⁻¹ indicates the attachment of the acrylamide species to the fatty fragment. The presence of the strong ester bands at 1740, 1245 and 1180 cm⁻¹ confirms the ester nature of the synthesized monomer (FIG. 3). FT-IR (film): 3400-3200 cm⁻¹ (N—H), 3010 (=CH, CH₂, alkene), 2870-2930 (CH₂, alkane), 1740 (C=O, ester), 1670 (C=O, amide 1), 1630 (C=C, vinyl), 1540 (N—H, amide II), 1245 (C—C(O)—O, ester), 1180 (C(O)—O—C, ester).

This unique approach for synthesizing a new soybean oil-based monomer is a one-step chemical reaction that not only utilizes commercially available, low cost monomer(s) and readily available soybean oil; it is also highly efficient, yielding 93% of product. The resulting soy-based monomer is highly reactive, due to the high reactivity of N-acryloyl (or N-methacryloyl) fragments in a conventional free radical polymerization process.

Example II. Free Radical Polymerization and Copolymerization

Our preliminary results indicate that the new SBM can be easily polymerized by conventional free radical polymerization resulting in soybean-based homopolymers, as well as copolymerized to form copolymers of SBM and vinyl monomers, including styrene, vinyl acetate, acrylates and methacrylates.

Figure 4:
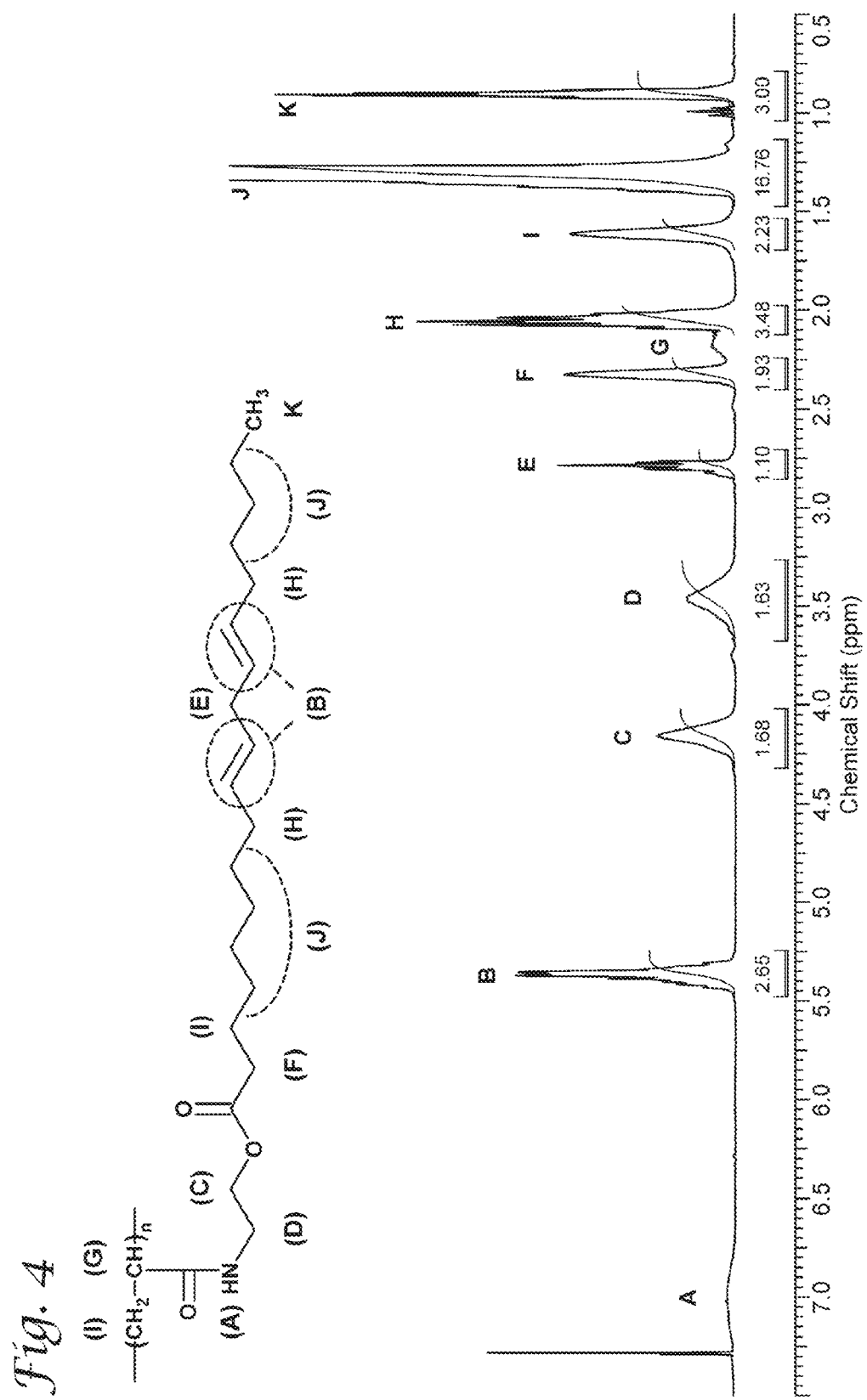
FIG. 4 shows a proton ($^1$H) NMR spectrum of a representative soybean oil based homopolymer.

The ¹H NMR spectrum of the homopolymer (FIG. 4), as compared with the ¹H NMR spectrum of the SBM (FIG. 1), shows the absence of the vinyl double bond of the acrylic functional group that confirms the formation of macrochains from the SBM monomer links. Hence, the homopolymer spectrum indicates that the polymer backbone is formed through the polymerization of SBM acrylic fragments, while the isolated double bonds of the soy-based monomer remain unaffected during the reaction.

Preliminary results show the SBM polymerizes better than commercially available acrylate fatty monomer-stearyl acrylate, and forms almost two times longer macromolecules in the same polymerization conditions.

SBM—Styrene Copolymer Synthesis

Into a solution of 7 g of SBM and 7 g of styrene dissolved in 40 ml of toluene, 0.05 g of 2-2'-azoisobutyronitrilc (AIBN) was added, then the nitrogen bubbling was done sufficiently to remove air. The reaction mixture was heated up to 80° C. and allowed to polymerize at this temperature for 5 hours. During polymerization reaction 1 ml* of 5 wt % AIBN solution in toluene was fed dropwise into the reaction mixture. After that, SBM-styrene copolymer was purified by precipitation with methanol.

SBM—MMA Copolymer Synthesis

Into a solution of 10 g of SBM and 5 g of methyl methacrylate (MMA) dissolved in 40 ml of toluene, 0.05 g of 2-2'-azoisobutyronitrile was added, then the nitrogen bubbling was done sufficiently to remove air. The reaction mixture was heated up to 80° C. and allowed to polymerize at this temperature for 5 hours. During polymerization process 1.5 ml* of 5 wt % AIBN solution in toluene was fed dropwise into reaction mixture. After reaction is complete SBM-methyl methacrylate copolymer was purified by precipitation with methanol.

*The amount of initiator solution may vary depending on the amount of stabilizer (2,6-Di-tert-butyl-4-methylphenol) present in SBM.

Example III

Soybean Oil Reactive Monomers for Bio-Based Latex Formation

Figure 5:
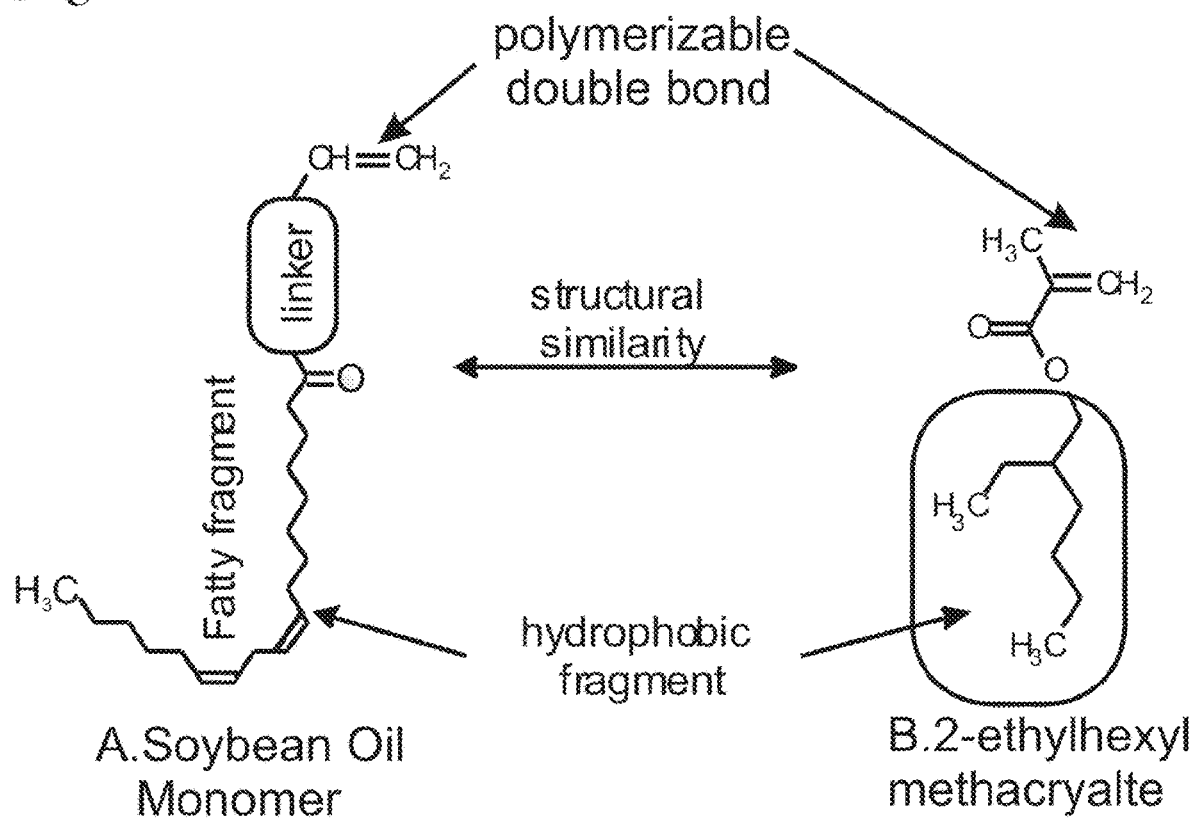
FIG. 5 shows the chemical structure of a representative soybean oil based monomer (SBM) (structure A) and commercially available petroleum-based 2-ethylhexyl methacrylate (structure B) used in latex manufacturing.

Soybean oil-based monomers (SBM) of the invention can be used in emulsion polymerization for bio-based latex formation. To the best of our knowledge, there is no open literature report on the preparation, properties and utilization of soybean oil-based acrylic monomers for free radical (emulsion) polymerization. No latexes are reported from soybean oil-based monomer as a single component in emulsion polymerization, or when it is employed in combination with acrylic monomers to produce bio-based latexes, Novel SBM-based waterborne latexes can be synthesized using emulsion polymerization. The presence of both a reactive (polymerizable) conjugated vinyl fragment (double bond) and a hydrophobic fatty acid fragment in the chemical structure (FIG. 5, structure A) is expected make the new SBM very attractive for the synthesis of polymeric latexes, in particular for paint production.

2-Ethylhexyl methacrylate (FIG. 5, structure B) is currently used as one of the main monomer (up to 70% wt) components in acrylic latex paint formulations. The advantage of this petroleum-based component is facile control over latex paint hydrophobicity and high (co)polymerization ability. The current price for this monomer at the market is, however, around $80/gallon. The use of the novel green component, SBM, in place of this currently widely applied hydrophobic monomer gives SBM a great advantage in potentially becoming one of the main components in latex paints. Moreover, we expect that the presence of fatty double bonds will encourage ambient self-crosslinking, which would further improve key properties and performance of the paints.

It is expected that this new monomer, which undergoes free radical polymerization, can be copolymerized with a range of commercially available vinyl monomers, such as methyl methacrylate, butylacrylate, 2-ethylhexyl methacrylate, and styrene, for example as comonomers for synthesis of new bio-based polymer latexes. Replacing all or part of the petroleum-based acrylic components in the latex with a natural ingredient is beneficial for a broad variety of materials, where paints and coatings are used. Advantageously, the properties of latexes and latex films can be adjusted or tuned by shifting the latex chemical composition from "no SBM in latex" to "maximum SBM content" or anywhere in between to obtain the desired performance. Using renewable feedstock will also have a positive economic impact within the manufacturing of coatings and paints.

Emulsion polymerization can be carried out to form new bio-based polymer latexes using one or more of the novel bio-based acrylic monomers. The soybean oil-based monomer can be employed as a single ingredient, or SBM can be used in combination with commercially available vinyl monomers (e.g., acrylates, methacrylates, styrene), widely used in industry for manufacturing latexes for paints and coatings.

The SBM was synthesized as in Example I and polymerized in free radical (co)polymerization with methyl methacrylate.

SBM—MMA Latex Synthesis

The following are introduced into a 250 ml reactor which is equipped with anchor stirrer, reflux condenser and thermostatically controlled jacket: 166 ml of DI water; 1.4 g of sodium dodecylsulfate; 70 g of SBM-MMA mixture (see Table 1 for SBM/MMA ratios).

TABLE 1

Poly(SBM-MMA) Latex Particles properties

| MMA/SBM, mol/mol | MMA/SBM, g/g | D, nm | $T_g$, °C. | $M_n$ | $M_w$ | PDI |
|---|---|---|---|---|---|---|
| 100/0 | 100/0 | 80 | 105 | 550,000 | 745,000 | 1.35 |
| 80/20 | 50/50 | 100 | 67.2 | 36,700 | 97,500 | 2.7 |
| 70/30 | 38/62 | 120 | 50.2 | 30,000 | 90,000 | 3.0 |
| 60/40 | 29/71 | 140 | 33.5 | 27,000 | 84,000 | 3.1 |
| 50/50 | 21/79 | 160 | 21.7 | 22,500 | 78,000 | 3.5 |
| 0/100 | 0/100 | 550 | −6.0 | 20,000 | 85,000 | 4.25 |

*denotes approximate values
**The initiator amount may be adjusted depending on the amount of stabilizer (2,6-Di-tert-butyl-4-methylphenol) present in SBM.

This mixture is heated up to 70° C. at slow stirring for 15 minutes, then sonicated (QSonica sonicator) for one minute, after that homogenized with a high-pressure homogenizer (5 passes were carried out). The miniemulsion obtained is composed of fine monomer droplets with mean diameter of the order of 40-150 nm. It is transferred into a 250 ml reactor which is equipped with anchor stirrer, reflux condenser and thermostatically controlled jacket. This miniemulsion is heated up to 70° C. The polymerization is initiated by addition of 0.3 g of potassium peroxodisulfate dissolved in 3 ml of water. Additionally 0.2 g** of potassium peroxodisulfate dissolved in 2 ml of water is added dropwise into the reaction mixture over the course of polymerization. The polymerization takes place in four hours.

After polymerization is done, a coagulum-free SBM-MMA latex is obtained. The latex characteristics are shown in Table 1.

SBM Reactivity in Free Radical Copolymerization

Further the reactivity of the SBM acrylic double bond and monomer feasibility in free radical copolymerization was evaluated. To this end, experiments were performed in order to determine the Q-e values for a new soy-based acrylic monomer.

For this purpose, in copolymerization of the SBM and styrene (St), the monomer reactivity ratios $r_1$ and $r_2$ were determined experimentally by measuring an instantaneous copolymer composition (with $^1$H NMR spectroscopy at low monomer conversions of 5-10%) (FIG. 6) and employing Mayo-Lewis copolymerization equation. Experimental data on $r_1$ and $r_2$ for SBM and St are shown in Table 2. Having the experimental $r_1$ and $r_2$ for SBM and St, as well as literature data on styrene Q-e values (Q=1 and e=−0.8), the Q-e of the SBM monomer was calculated. This calculation yields Q=0.39 and e=0.58.

TABLE 2

Monomer reactivity ratios for copolymerization of SBM and methyl methacrylate (MMA), styrene (St), and vinyl acetate (Vac).

| Comonomer pair | $r_1$ | $r_2$ |
|---|---|---|
| SBM-St | 0.18 ± 0.06* | 0.85 ± 0.2* |
| SBM-MMA | 0.45 ± 0.1 | 2.15 ± 0.4 |
| SBM-Vac | 9.43 ± 0.7 | 0.06 ± 0.01 |

*Determined experimentally.
**Calculated using the Q-e values.

To demonstrate that the Q-e values of SBM can be applied to control copolymer composition, additional studies on copolymerization of the soy-based acrylic monomer with methyl methacrylate (MMA) and vinyl acetate (Vac) were performed.

The chemical composition of each resulting SBM-MMA and SBM-Vac copolymer (ten for each monomer pair) was determined experimentally using $^1$H NMR spectroscopy and compared to the theoretical copolymer compositions. The theoretical compositions were assessed using the Alfrey-Price scheme and the Q-e values for MMA (Q=0.78, e=0.4), Vac (Q=0.026, e=−0.22), and SBM (Q=0.39, e=0.58) to determine $r_1$ and $r_2$ for the SBM-MMA and SBM-Vac monomer pairs. In the next step, these $r_1$ and $r_2$ were applied to calculate each theoretical copolymer composition using the Mayo-Lewis copolymerization equation.

Figure 6:
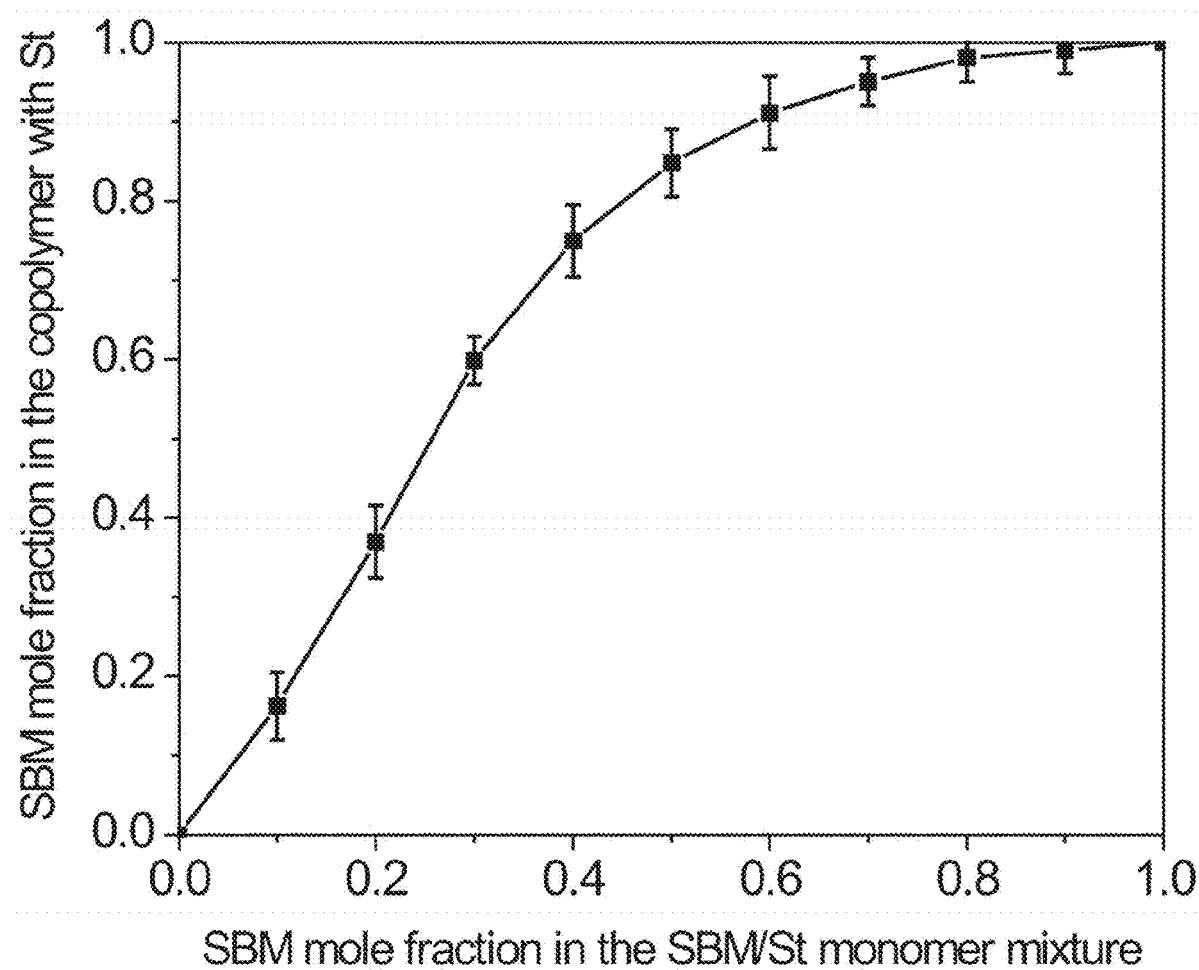
FIG. 6 shows experimental SBM content in an SBM-St copolymer vs. SBM content in an initial feed mixture.
Figure 7A:
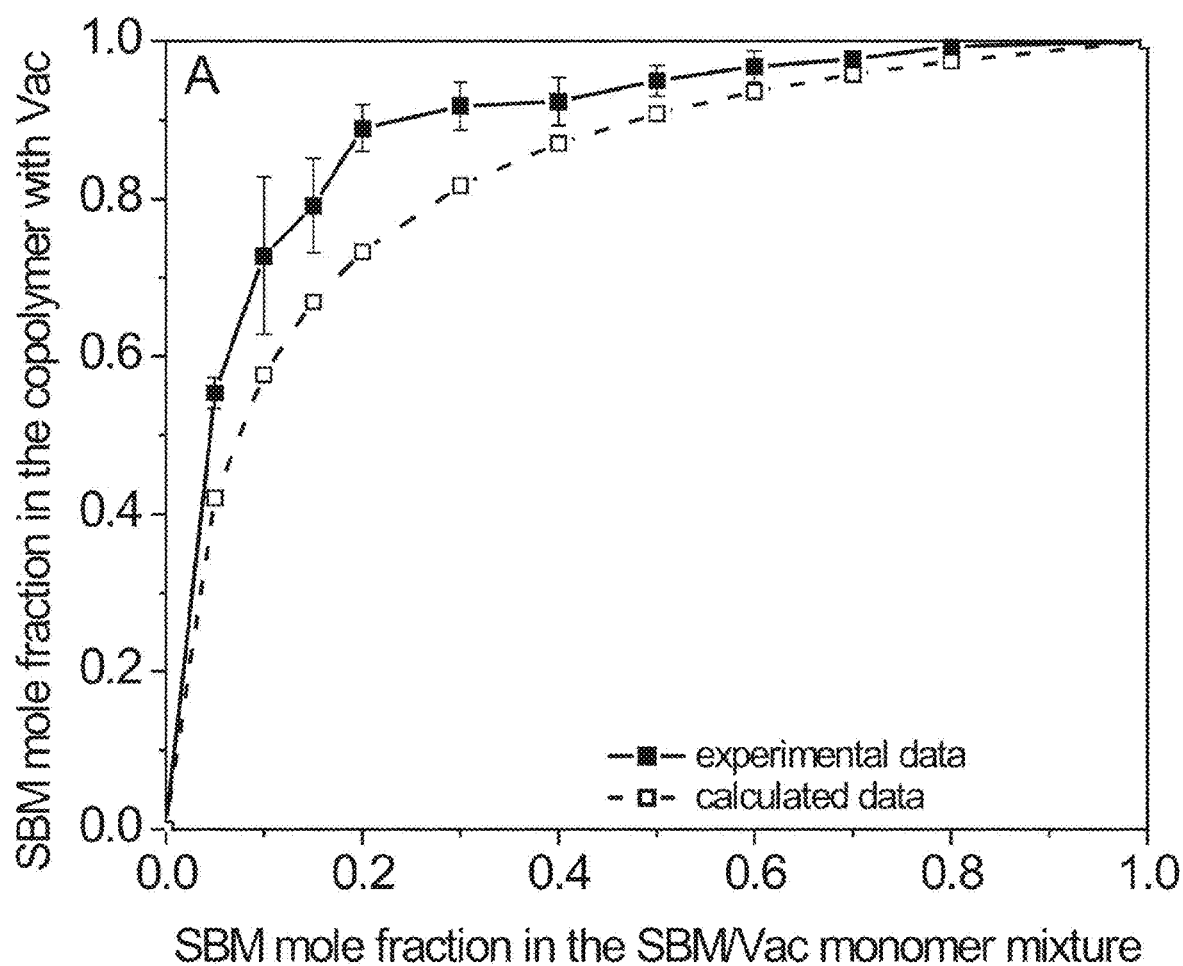
FIG. 7A shows calculated and experimental SBM content in SBM-Vac vs. SBM content in the initial feed mixture.
Figure 7B:
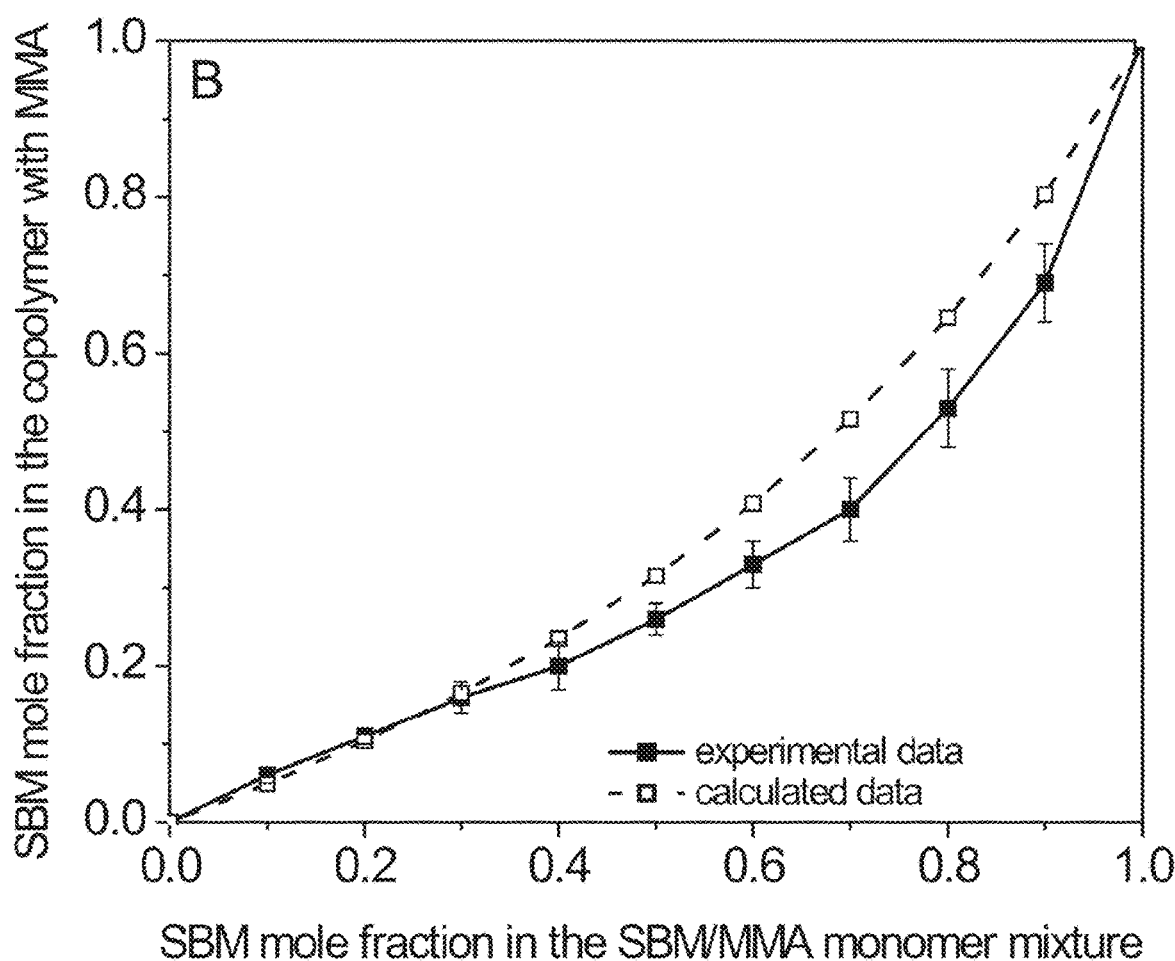
FIG. 7B shows calculated and experimental SBM content in SBM-MMA copolymer composition vs. SBM content in the initial feed mixture.

It can be clearly seen in FIG. 6 that the experimental and calculated plots are in good agreement, indicating that copolymerization of SBM with Vac (FIG. 7A) and MMA (FIG. 7B) can be described with the classical Mayo-Lewis copolymerization equation. Additionally, the Q-e values of the new monomer allow the prediction of SBM reactivity in free radical copolymerization with other monomers.

To show that the fraction of the SBM monomer units in the resulting macromolecules affects the copolymers' properties, the glass transition temperature ($T_g$) of the SBM-MMA copolymers with a varied composition was determined using differential scanning calorimetry (DSC). The DSC data indicate that $T_g$ of the SBM-MMA copolymers changes considerably with increases in the fraction of the soybean oil-derived fragments in the synthesized macromolecules, approaching 22° C. when the copolymer contains 30 mol % of SBM monomer units (FIG. 8).

Figure 8:
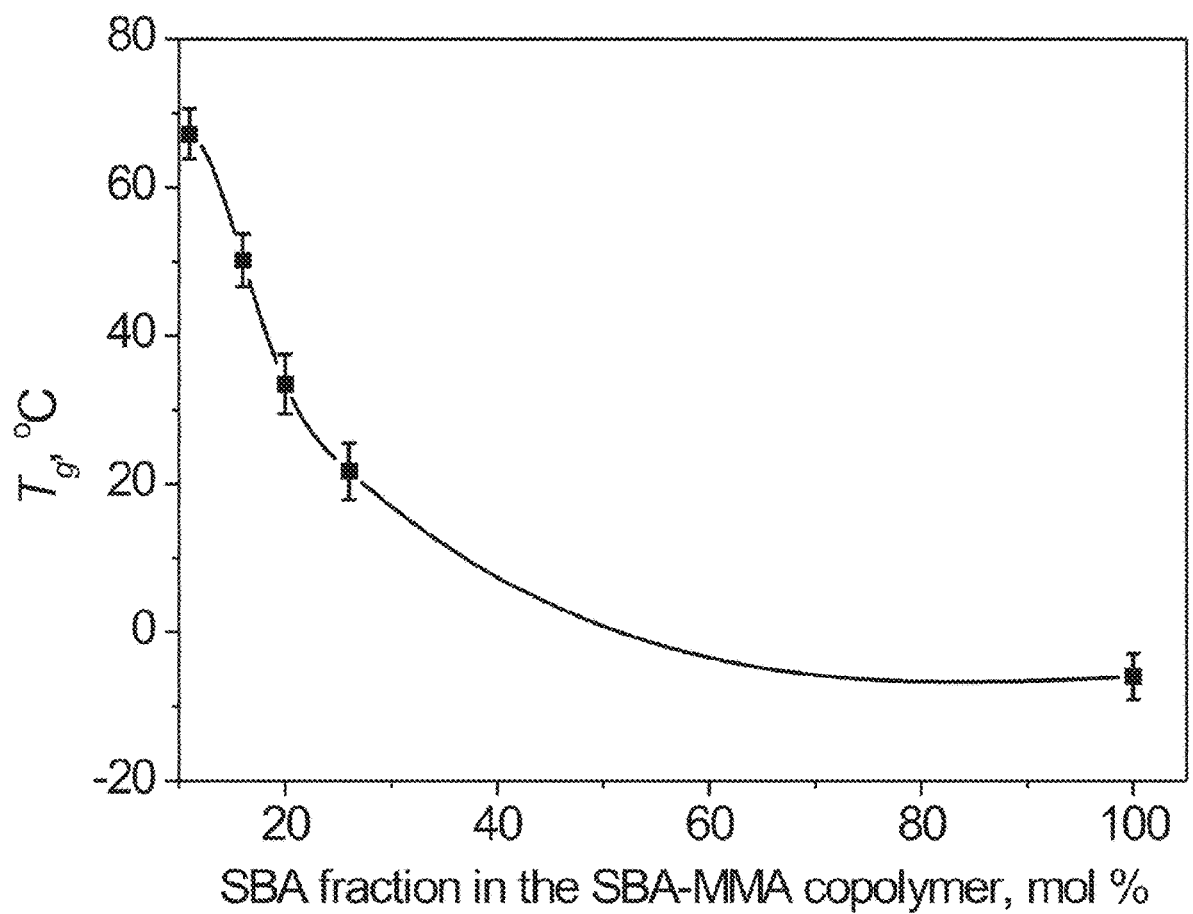
FIG. 8 shows glass transition temperature ($T_g$) of SBM-MMA copolymers vs. soybean oil-derived fragment content in the macromolecular backbone determined with differential scanning calorimetry (DSC).

FIG. 8 shows the DSC data indicating that $T_g$ of the SBM-MMA copolymers changes considerably by increasing fraction of the soybean oil-derived fragments in the synthesized macromolecules.

The results achieved thus indicate that replacing petroleum-based monomers in latexes with the new soybean oil-based monomer is feasible. Shown below are the chemical structures of three exemplary SBM-based copolymers synthesized.

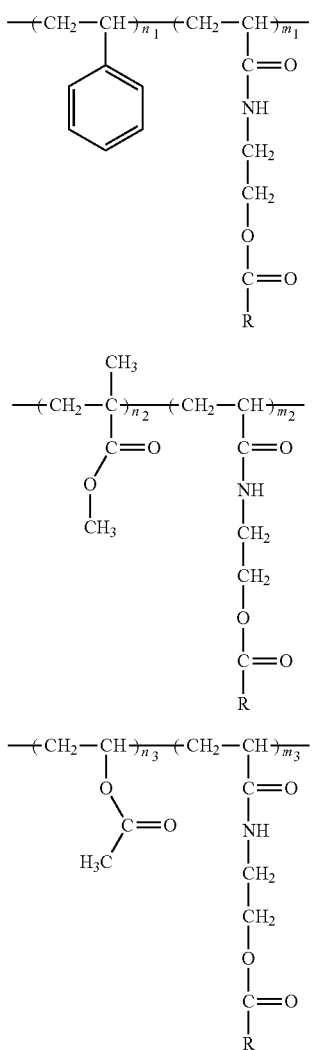

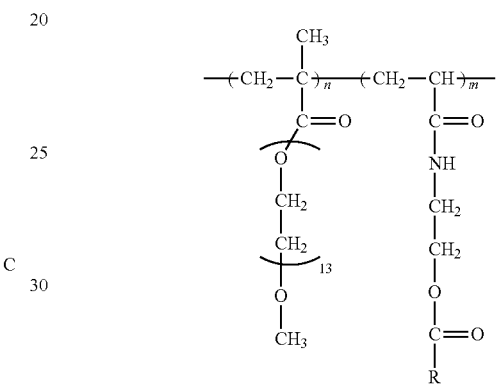

These structures represent the chemical structure of the copolymers from the soy-based acrylic monomer and (A) styrene (SBM-St); (B) methyl methacrylate (SBM-MMA); and (C) vinyl acetate (SBM-Vac). R refers to the fatty acid chains present in the soybean oil, and thus is inclusive of any of the various fatty chains present in the soybean oil. The values for m and n can vary depending on the comonomers used, the characteristics of polymer desired and the relative feed mixtures. Changes in the monomer feed mixture can be used to vary the copolymer composition and thus the values for m and n. See, for example, FIGS. 6, 7A and 7B. In some embodiments, values for m and n can independently range from 1:1000 to 1000:1 mass parts in terms of chemical composition of resulting macromolecules.

SBM-MPEG MA Copolymers Synthesis

To synthesize SBM-MPEG MA copolymer, SBM (0.005 M), methoxy poly(ethylene glycol) methacrylate (MPEG550MA, molecular weight 550 g/mol, Bisomer, referred to herein as MPEG MA) (0.005 M) and A1BN (0.012 M) were dissolved in toluene. The reaction mixture was purged with argon at room temperature for 30 min. The copolymerization was carried out under an argon blanket at 60° C. for 4-24 h until a total monomer conversion of 80-90% was reached. The resulting copolymer was isolated by precipitation in hexane and purified by multiple re-precipitations from toluene/hexane mixture. Finally, the purified polymer was dried under reduced pressure at room temperature until a constant weight was obtained. The resulting copolymer, containing 50 mol % SBA monomer units, was soluble in toluene, THF and water with limited solubility in acetone, benzene and methanol.

SBM-MPEG MA Copolymers Surface Activity

The chemical structure of the SBM-MPEG MA copolymer is depicted below. Surfactant molecules typically contain both hydrophobic and hydrophilic moieties, thereby making them amphiphilic and allowing for the formation of micelles (molecular aggregates) in water. The molecular aggregates are able to take up dirt (e.g., oil) and provide the cleaning performance often attributable to surfactants in personal care applications, for example as in soaps, shampoos, facial and body cleansers, and the like.

Figure 9A:
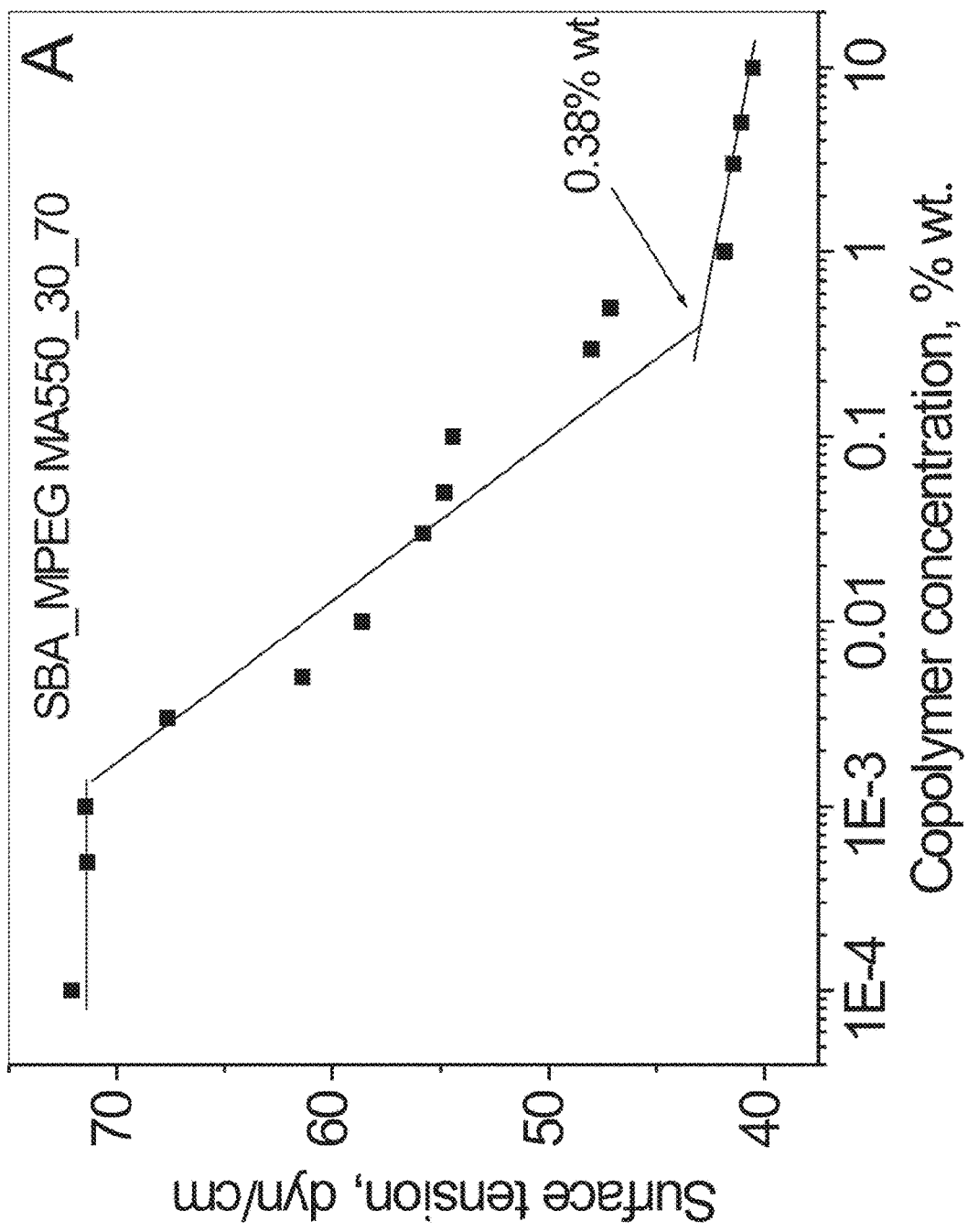
FIG. 9A shows surface tension in SBA-MPEG MA solutions vs. SBA-MPEG MA concentration for copolymer containing 30 wt % of bio-based monomer fragments.

Free radical copolymerization was applied as described above to synthesize a random copolymer from SBM units as the hydrophobic fragments and MPEG MA fragments acting as hydrophilic moieties in the SBM-MPEG MA macromolecules. FIG. 9A shows that SBM-MPEG MA copolymer decreases surface tension of water, thus, their macromolecules are indeed amphiphilic and provide surface activity to SBM-MPEG MA aqueous solutions.

Figure 9B:
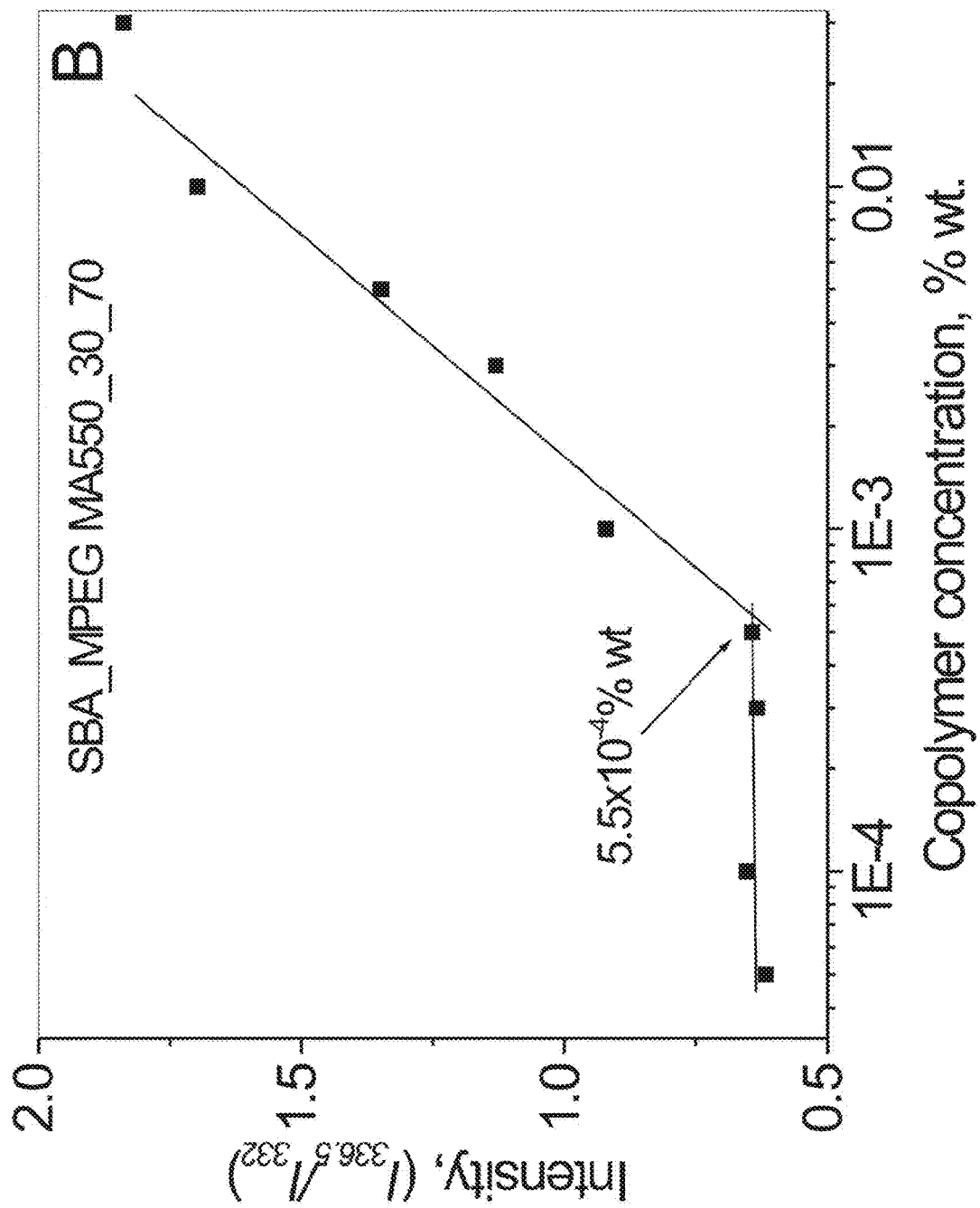
FIG. 9B shows the intensity ratio of the excitation spectra of pyrene in SBA-MPEG MA solutions vs. SBA-MPEG MA concentration for copolymer containing 30 wt % of bio-based monomer fragments.

To confirm formation of SBM-MPEG MA micelles in aqueous solution, critical micelle concentration was measured using solubilization of pyrene, fluorescent probe molecules for studying the association behavior of amphiphilic macromolecules. A red shift of the absorption band with enhanced excitation intensity was observed in optical spectra measurements due to the migration of the probe from the hydrophilic to the hydrophobic region of the polymer micelles, indicating the formation of SBPS micelles at critical micelle concentration (cmc) $5.5\times10^{-4}\%$ wt. (FIG. 9B).

The complete disclosures of all patents, patent applications including provisional patent applications, publications including patent publications and nonpatent publications, and electronically available material (including, for example, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A polymer comprising at least one bio-based acrylic monomer comprising:
   a bio-derived fatty acyl group comprising a carbonyl group, wherein the fatty acyl group comprises at least 1 double bond; and
   an acrylic group, wherein the acrylic group comprises an acrylamide group or a methacrylamide group;
   wherein the acrylic group is esterically linked, directly or indirectly, to the fatty carbonyl group.

2. The polymer of claim 1 wherein the bio-based acrylic monomer has formula (I):

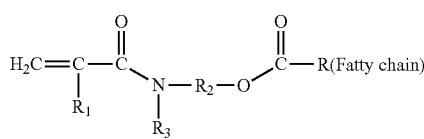

wherein R is a fatty chain derived from a plant oil or an animal fat;
R1 and R3 are each independently H, an aliphatic group, or an aromatic group; and
R2 is a divalent aliphatic group or aromatic group.

3. The polymer of claim 1 comprising a homopolymer of the bio-based acrylic monomer or a copolymer further comprising at least one comonomer.

4. The polymer of claim 3 wherein the comonomer comprises a vinyl comonomer.

5. The polymer of claim 3 wherein the comonomer is selected from the group consisting of an acrylate, a methacrylate, an acrylamide, a methacrylamide, and an acrylonitrile.

6. The polymer of claim 3 wherein the comonomer is selected from the group consisting of an alkyl acrylate and an alkyl methacrylate.

7. The polymer of claim 3 wherein the comonomer is selected from the group consisting of a 1,3-butadiene, a butyl acrylate, a butyl methacrylate, an ethyl acrylate, a hydroxyethyl acrylate, an isoprene, a maleic anhydride, a methyl acrylate, a methyl methacrylate, a 2-ethylhexyl methacrylate, a styrene, a vinyl acetate, a vinyl ether, a vinyl pyridine, a vinyl chloride, a poly(ethylene glycol) methacrylate, a poly(ethylene glycol) methyl ether methacrylate, a poly(ethylene glycol) methyl ether acrylate, a phenyl ether acrylate, and a polyfunctional vinyl monomer.

8. The polymer of claim 1 formed in a free radical polymerization reaction.

9. A latex comprising an emulsion comprising a polymer comprising the bio-based acrylic monomer of claim 1.

10. A waterborne coating comprising a polymer comprising the bio-based acrylic monomer of claim 1.

11. A paint, adhesive, thermoplastic, plastic, resin, emulsion, surfactant, gel, coating or oil comprising a polymer comprising the bio-based acrylic monomer of claim 1.

12. An article comprising a latex, waterborne coating, paint, adhesive, thermoplastic, plastic, resin, emulsion, surfactant, gel, coating or oil comprising a polymer comprising the bio-based acrylic monomer of claim 1.

13. A personal care product comprising the polymer of claim 1.

14. An industrial cleaning product comprising the polymer of claim 1.

15. The polymer of claim 2 wherein $R_1$ is H or a $(C_1$-$C_{10})$alkyl.

16. The polymer of claim 2 wherein $R_2$ is a $(C_1$-$C_{10})$ alkylene, an alkylene glycol, or a polyalkylene glycol.

17. The polymer of claim 2 wherein $R_3$ is H or a $(C_1$-$C_{10})$alkyl.

18. The polymer of claim 1 wherein the fatty acyl group comprises a $C_5$-$C_{21}$ alkyl group or a $C_5$-$C_{21}$ alkenyl group.

19. The polymer of claim 1 wherein the fatty acyl group comprises 1, 2, 3, 4, 5 or 6 double bonds.

* * * * *

UNITED STATES PATENT AND TRADEMARK OFFICE
CERTIFICATE OF CORRECTION

PATENT NO. : 10,584,094 B2  
APPLICATION NO. : 16/395755  
DATED : March 10, 2020  
INVENTOR(S) : Voronov et al.

Page 1 of 1

It is certified that error appears in the above-identified patent and that said Letters Patent is hereby corrected as shown below:

On the Title Page

Column 2, under OTHER PUBLICATIONS, first reference, first line, "fatty add" should read --fatty acid--.

In the Specification

Column 2, Line 44, "entericlly" should read --esterically--.

Column 2, Line 48, "enterically" should read --esterically--.

Column 3, Line 62, "include" should read --includes--.

Column 3, Line 66, "include" should read --includes--.

Signed and Sealed this  
Twenty-third Day of March, 2021

Drew Hirshfeld  
*Performing the Functions and Duties of the*  
*Under Secretary of Commerce for Intellectual Property and*  
*Director of the United States Patent and Trademark Office*